(12) United States Patent
Voelkel et al.

(10) Patent No.: US 10,626,166 B2
(45) Date of Patent: Apr. 21, 2020

(54) DETECTION OF CHO-MIF CONTAMINATIONS

(71) Applicants: Baxalta GmbH, Glattpark (Opfikon) (CH); Baxalta Incorporated, Bannockburn, IL (US)

(72) Inventors: Dirk Voelkel, Vienna (AT); Patrice Douillard, Vienna (AT); Gerhard Antoine, Gross-Enzersdorf (AT); Randolf Kerschbaumer, Klosterneuburg (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 15/505,894

(22) PCT Filed: Aug. 21, 2015

(86) PCT No.: PCT/EP2015/069231
§ 371 (c)(1),
(2) Date: Feb. 22, 2017

(87) PCT Pub. No.: WO2016/026956
PCT Pub. Date: Feb. 25, 2016

(65) Prior Publication Data
US 2018/0215807 A1 Aug. 2, 2018

Related U.S. Application Data

(60) Provisional application No. 62/040,933, filed on Aug. 22, 2014.

(51) Int. Cl.
*G01N 33/68* (2006.01)
*C07K 16/06* (2006.01)
*C07K 16/24* (2006.01)

(52) U.S. Cl.
CPC ............ *C07K 16/065* (2013.01); *C07K 16/24* (2013.01); *G01N 33/6863* (2013.01); *C07K 2317/14* (2013.01); *C07K 2317/30* (2013.01)

(58) Field of Classification Search
None
See application file for complete search history.

(56) References Cited

U.S. PATENT DOCUMENTS

| | | | | |
|---|---|---|---|---|
| 5,350,687 | A * | 9/1994 | Odink | C07K 14/52 435/335 |
| 9,465,037 | B2 * | 10/2016 | Kerschbaumer | C07K 16/24 |
| 2012/0171699 | A1 * | 7/2012 | Goodman | C07K 16/00 435/7.21 |

FOREIGN PATENT DOCUMENTS

| | | |
|---|---|---|
| WO | WO 2009/086920 | 7/2009 |
| WO | WO 2013/050453 | 4/2013 |
| WO | WO 2013/050457 A1 * | 4/2013 |

* cited by examiner

*Primary Examiner* — Elizabeth C. Kemmerer
(74) *Attorney, Agent, or Firm* — Morgan, Lewis & Bockius LLP

(57) ABSTRACT

The invention concerns a detection method to enable the detection of complexes formed between antibodies and antigen which is endogenous to the production cell line, e.g. CHO MIF in a final product.

12 Claims, 5 Drawing Sheets

Specification includes a Sequence Listing.

DETECTION OF CHO-MIF CONTAMINATIONS

Based on the identification and characterization of the CHO-MIF gene and the provision of CHO-MIF knock-out cells, the present invention is directed to a highly sensitive detection method of specific CHO-MIF complexes and of free soluble CHO-MIF, particularly in the production of anti-MIF antibodies, which allows the detection of CHO-MIF contaminations and thus assists the provision of a highly pure antibody preparation. The present invention is therefore also concerned with the provision of advantageous monoclonal rabbit antibodies which can be used for a CHO-MIF detection method. In a preferred embodiment, the antibody is an anti-(ox)MIF antibody.

BACKGROUND

Macrophage migration inhibitory factor (MIF) is a cytokine initially isolated based upon its ability to inhibit the in vitro random migration of peritoneal exudate cells from tuberculin hypersensitive guinea pigs (containing macrophages) (Bloom et al. Science 1966, 153, 80-2; David et al. PNAS 1966, 56, 72-7). Today, MIF is known as a critical upstream regulator of the innate and acquired immune response that exerts a pleiotropic spectrum of activities.

The human MIF cDNA was cloned in 1989 (Weiser et al., PNAS 1989, 86, 7522-6), and its genomic localization was mapped to chromosome 22. The product of the human MIF gene is a protein with 114 amino acids (after cleavage of the N-terminal methionine) and an apparent molecular mass of about 12.5 kDa. MIF has no significant sequence homology to any other protein. The protein crystallizes as a trimer of identical subunits. Each monomer contains two antiparallel alpha-helices that pack against a four-stranded beta-sheet. The monomer has additional two beta-strands that interact with the beta-sheets of adjacent subunits to form the interface between monomers. The three subunits are arranged to form a barrel containing a solvent-accessible channel that runs through the center of the protein along a molecular three-fold axis (Sun et al. PNAS 1996, 93, 5191-5196).

It was reported that MIF secretion from macrophages was induced at very low concentrations of glucocorticoids (Calandra et al. Nature 1995, 377, 68-71). However, MIF also counter-regulates the effects of glucocorticoids and stimulates the secretion of other cytokines such as tumor necrosis factor TNF-α and interleukin IL-1 β (Baugh et al., Crit Care Med 2002, 30, S27-35). MIF was also shown e.g. to exhibit pro-angiogenic, pro-proliferative and anti-apoptotic properties, thereby promoting tumour cell growth (Mitchell, R. A., Cellular Signalling, 2004. 16(1): p. 13-19; Lue, H. et al., Oncogene 2007. 26(35): p. 5046-59). It is also e.g. directly associated with the growth of lymphoma, melanoma, and colon cancer (Nishihira et al. J Interferon Cytokine Res. 2000, 20:751-62).

MIF is a mediator of many pathologic conditions and thus associated with a variety of diseases including inter alia inflammatory bowel disease (IBD), rheumatoid arthritis (RA), acute respiratory distress syndrome (ARDS), asthma, glomerulonephritis, IgA nephropathy, myocardial infarction (MI), sepsis and cancer, though not limited thereto.

Polyclonal and monoclonal anti-MIF antibodies have been developed against recombinant human MIF (Shimizu et al., FEBS Lett. 1996; 381, 199-202; Kawaguchi et al, Leukoc. Biol. 1986, 39, 223-232, and Weiser et al., Cell. Immunol. 1985, 90, 16778). Anti-MIF antibodies have been suggested for therapeutic use. Calandra et al, (J. Inflamm. 1995. 47, 39-51) reportedly used anti-MIF antibodies to protect animals from experimentally induced gram-negative and gram-positive septic shock. Anti-MIF antibodies were suggested as a means of therapy to modulate cytokine production in septic shock and other inflammatory disease states. Glycosylation-inhibiting factor (GIF) is a protein described by Galat et al. (Eur. J. Biochem, 1994, 224, 417-21). MIF and GIF are now recognized to be identical Watarai et al. (PNAS 2000, 97, 13251-6) described polyclonal antibodies binding to different GIF epitopes to identify the biochemical nature of the posttranslational modification of GIF in Ts cells.

In view of the clear biological significance of MIF/GIF, it is therefore necessary and would be highly desirable to provide purified anti-MIF antibodies as diagnostic and therapeutic tools.

Clearly, therefore a need exists for the production of anti-MIF antibodies, whereby these are free from contaminations.

SUMMARY OF THE INVENTION

Various methods for the production of anti-(h)MIF antibodies are currently available. One major approach is to use the recombinant production of anti-(h)MIF antibodies whereby a host cell expresses the desired anti-(h)MIF antibody product.

Chinese hamster ovary (CHO) cells are a cell line derived from the ovary of the Chinese hamster (*Cricetulus griseus*). They are frequently and broadly used in biological and medical research production of therapeutic proteins, e.g. antibodies.

Today, CHO cells are the most commonly used mammalian hosts for industrial production of recombinant protein therapeutics, including antibodies.

CHO cells have been a cell line of choice because of their rapid growth and high protein production. They have become the mammalian equivalent of *E. coli* in research and biotechnology today, especially when long-term, stable gene expression and high yields of proteins are required.

Independent of the choice of host cell, it is consistently necessary to purify a desired therapeutic antibody after its production by the host cell. In particular, the expressed antibody is e.g. present in cell culture supernatants which are contaminated with other proteins, and quite frequently with the antigen itself and/or antigen/antibody complexes. The antigen itself is produced by the host cell line e.g. endogenously. For further cell lines, which are used for the production of antibodies, similar issues exist as for the above described CHO cell line. Furthermore, the present inventors, upon investigation of a possible preferable production and purification process of anti-(h)MIF antibodies with the use of CHO cells as host cells had additionally discovered that CHO cells themselves produce MIF. MIF is an ubiquitous molecule. It has been shown that further cell lines, e.g. HEK cells, also produce a MIF, which is typical for the respective cell line. The MIF as produced by CHO cells is a Chinese hamster MIF, due to the fact that CHO cells are derived from ovary cells of a Chinese hamster. This "Chinese hamster-MIF" (in the following and above also designated as "CHO-MIF"), possibly because of the high homology between CHO-MIF and other, e.g. human, MIF also binds to the anti-(h)MIF antibodies to be produced. Thus, endogenous CHO-MIF could possibly contaminate the final CHO-cell based preparations of antibodies directed to non-CHO-MIF (e.g. complexed to the desired anti-(h)MIF antibodies), like e.g. human MIF (hMIF), or mouse MIF (mMIF).

An anti-MIF antibody can be an anti-(h)oxMIF antibody and both terms are used interchangeably here. Therefore, there exists a need for the provision of a sensitive method to detect minor amounts of CHO-MIF contaminations in preparations of anti-(h)MIF antibodies produced in CHO cells, which produce CHO-MIF.

DETAILED DESCRIPTION OF THE INVENTION

The present invention is directed to the detection of impurities, in particular CHO-MIF impurities, and ensures an effective and superior product after purification of antibodies, in particular anti-(h)MIF antibodies, or antigen binding portions thereof from cell cultures. In a preferred embodiment, the antibody is an anti-(h)MIF antibody. A highly sensitive detection method of specific CHO-MIF complexes, particularly in the production of anti-(h)MIF antibodies, is provided and allows the detection of CHO-MIF contaminations and thus assists in the provision of a highly pure antibody preparation. The present invention is therefore also concerned with the provision of an advantageous monoclonal rabbit antibody which can be used for a CHO-MIF detection method and a detection method using the same. The present invention is thus equally concerned with a method for the production and/or purification of an anti-(h)MIF antibody wherein the hereinbefore and hereinbelow described detection method is used as a quality control step. The quality control step described herein can be used at any stage during production or purification of an anti-(h)MIF antibody. Preferably, this step is part of the quality control of a production method for an anti-(h)MIF antibody and is used after the cultivation in the CHO cells has been finalized. Most preferably, this quality control step is used as the detection step for CHO MIF in the final product preparation.

Independent of the choice of host cell, it is consistently necessary to purify a desired therapeutic antibody after its production by the host cell. In particular, the expressed antibody is e.g. present in cell culture supernatants which are contaminated with other proteins, and quite frequently with the antigen itself or antigen/antibody complexes. The antigen itself is produced by the host cell line e.g. endogenously. It is thus important to conduct a detection step for these impurities as a quality control step in such a purification process to ensure that no such contaminations remain.

The present monoclonal antibodies are capable of detecting CHO MIF contaminations down to a level of less than 0.03125 ppm.

Figure 1A:
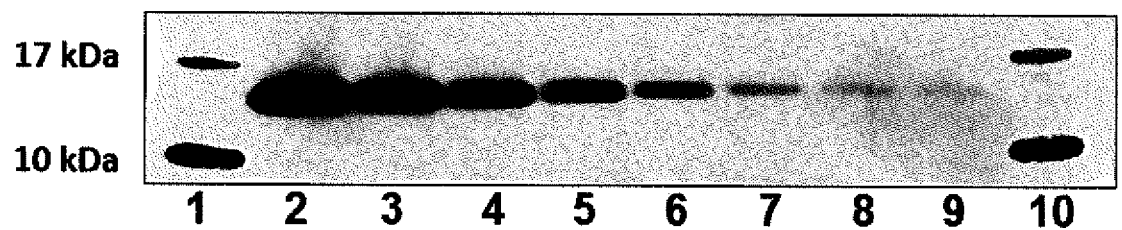
FIG. 1a: shows a Western Blot with different amounts of recombinant CHO-MIF protein detected by the monoclonal rabbit anti CHO-MIF antibody. After the incubation with the monoclonal rabbit anti CHO-MIF antibody, a commercial available horse radish peroxidase (HRP) conjugated donkey anti rabbit IgG was used in combination with the commercial HRP substrate (Super Signal West Femto Maximum Sensitivity Substrate; Pierce, Cat. NO. 34095). The resultant CHO-MIF signals were scanned by a LAS4000 Image Reader and directly quantified by the Image Quant LAS4000 software.
Figure 1B:
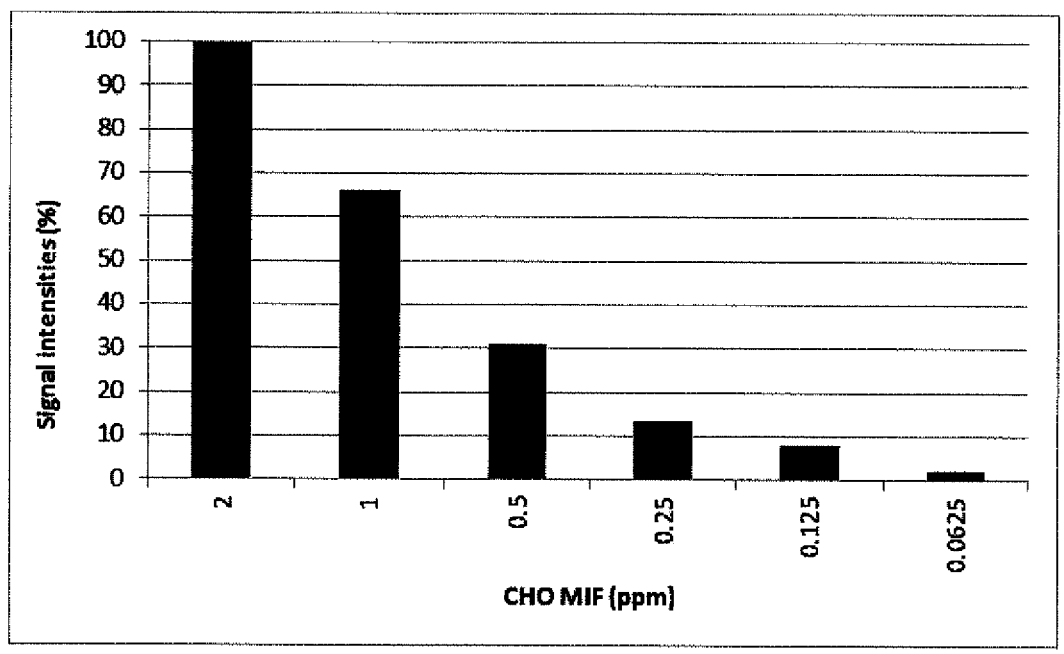

This Western Blot demonstrates the very surprisingly increased and advantageous sensitivity by using the monoclonal rabbit anti CHO-MIF antibody down to 0.03125 ng CHO-MIF (lane 9) which is corresponding to 0.0625 ppm CHO-MIF impurity in 500 µg human anti-MIF antibodies:

1 &10: Molecular weight marker;
2: 4 ng CHO-MIF (=8 ppm in 500 µg/mL anti human MIF antibody solution);
3: 2 ng CHO-MIF (=4 ppm in 500 µg/mL anti human MIF antibody solution);
4: 1 ng CHO-MIF (=2 ppm in 500 µg/mL anti human MIF antibody solution);
5: 0.5 ng CHO-MIF (=1 ppm in 500 µg/mL anti human MIF antibody solution);
6: 0.25 ng CHO-MIF (=0.5 ppm in 500 µg/mL anti human MIF antibody solution);
7: 0.125 ng CHO-MIF (=0.25 ppm in 500 µg/mL anti human MIF antibody solution);
8: 0.0625 ng CHO-MIF (=0.125 ppm in 500 µg/mL anti human MIF antibody solution);
9: 0.03125 ng CHO-MIF (=0.0625 ppm in 500 µg/mL anti human MIF antibody solution);

FIG. 1b: is a bar chart of the CHO-MIF protein signals resultant from a Western Blot as shown in FIG. 1a. The signal from the 2 ppm CHO-MIF was set to 100% and directly compared to the other CHO-MIF signals resultant from the scanner software.

2 ppm CHO-MIF signal is corresponding to 1 ng CHO-MIF impurity in 500 µg human anti-(h)MIF antibodies; 1 ppm CHO-MIF is corresponding to 0.5 ng CHO-MIF impurity in 500 µg human anti-(h)MIF antibodies; 0.5 ppm is corresponding to 0.25 ng CHO-MIF impurity in 500 µg human anti-(h)MIF antibodies etc.

These figures demonstrate the obviously increased sensitivity by using the monoclonal rabbit anti CHO-MIF antibody up to 0.0625 ppm (=0.03125 ng) CHO-MIF impurity in 500 µg human anti-(h)MIF antibodies.

Figure 2:
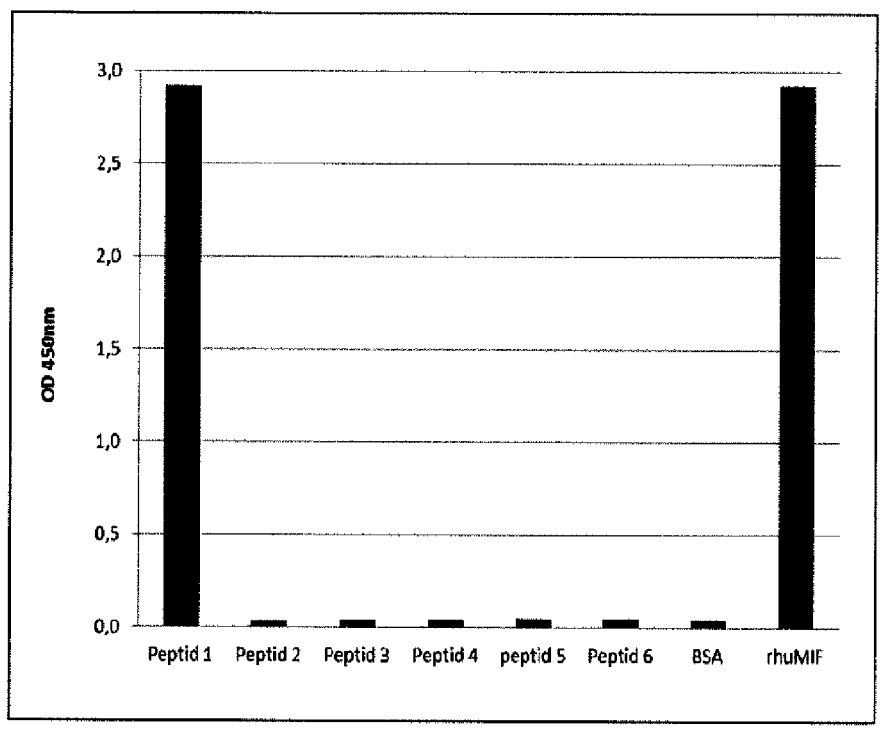

FIG. 2: shows the results from the epitope mapping of the monoclonal rabbit anti CHO-MIF antibody by an ELISA. To that avail, 6 peptides (each 34mer) corresponding to the published huMIF sequence as well as bovine serum albumin (BSA) and full length recombinant human MIF as controls were added to an ELISA plate and incubated over night at 4° C. After washing steps, the rabbit antibodies were added at a concentration of 500 ng/mL and incubated for 2 hours at room temperature. After additional washing steps, the monoclonal antibodies were detected by a commercial goat anti rabbit HRP conjugated and TMB as substrate. The signals were read out after stopping of the 30 min color change reaction at 450 nm. The epitope mapping by ELISA demonstrate the binding region of the monoclonal rabbit anti CHO-MIF at the N-terminus to MIF (peptide 1). (Black bars: show the signals of the monoclonal rabbit anti CHO-MIF antibody to the MIF peptides).

Figure 3:
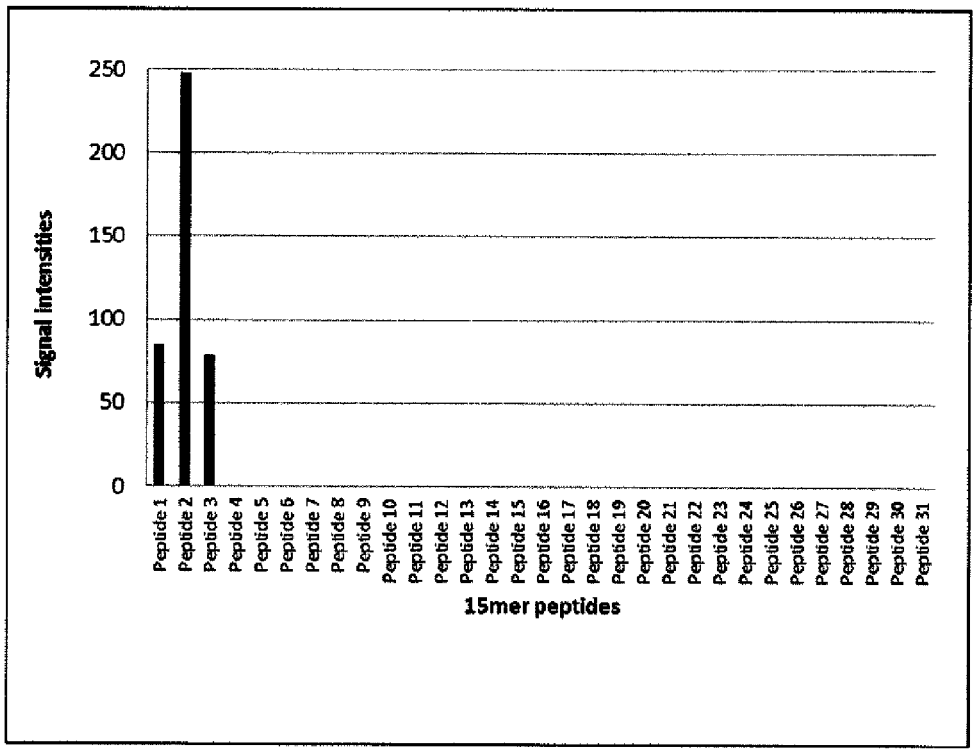

FIG. 3: shows the epitope mapping of the monoclonal rabbit anti CHO-MIF antibody A5 by microarray technology. To that avail, 15mers of peptides (shifted by 4 aa, respectively, starting with the first amino acid) corresponding to the huMIF sequence were spotted on a glass slide in triplicates. For this experiment the monoclonal rabbit anti CHO-MIF antibody was labeled by Cy5 (cyanine dye) (commercial kit from GE Healthcare). This conjugate was applied at a concentration of 10 µg/mL at the glass slides for 2 hours. After washing steps the slides were dried and analyzed by a microarray scanner (ScanArray G Plus from Perkin Elmer) at 633 nm. The signal intensity of each 15mer peptide is shown as black bars in the FIG. 3. The figure demonstrates the specific binding of the monoclonal rabbit anti CHO-MIF antibody to the N-terminal part of MIF.

(Black bars: monoclonal rabbit anti CHO-MIF antibody; data calculated by the mean of three subarrays).

Figure 4:
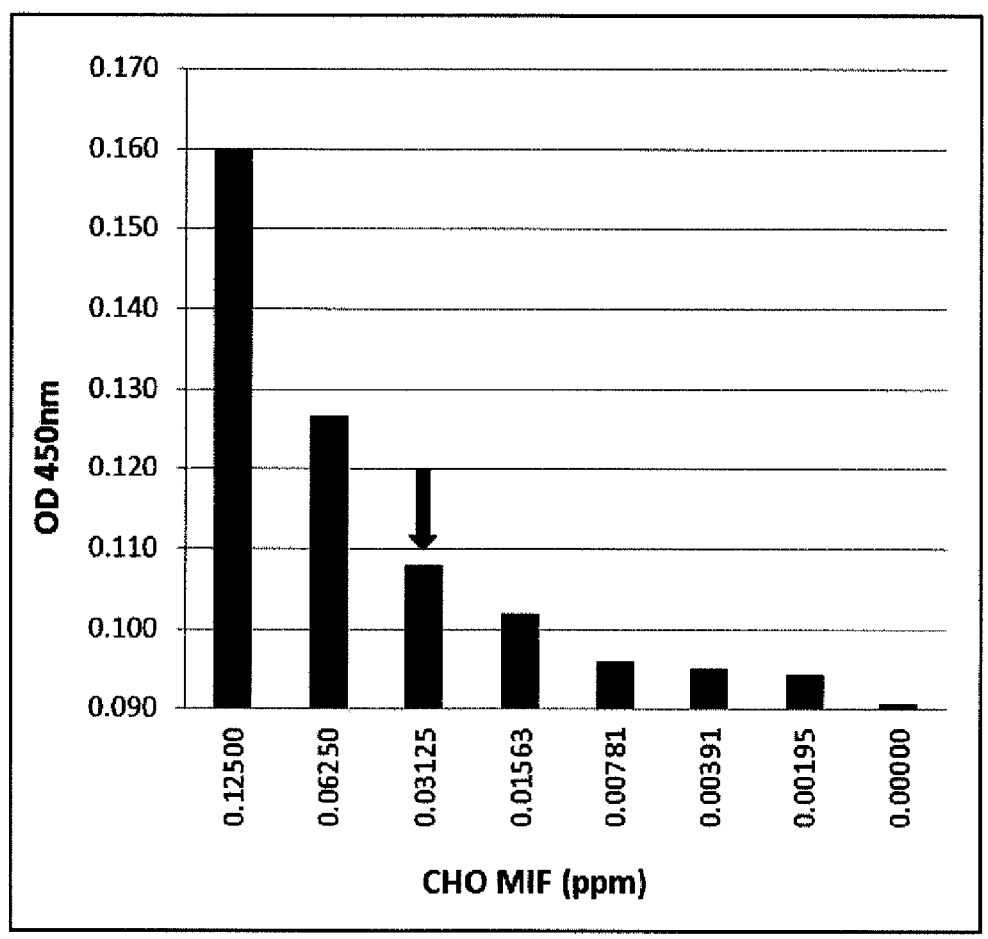

FIG. 4: Determination of LOD and LOQ (ELISA);

FIG. 4 is a bar chart of different concentrations of recombinant CHO-MIF signals in the presence of 20 mg/ml anti human MIF antibody resultant from a CHO-MIF ELISA. The LOD (limit of detection) defined as 3× standard deviation of the blank was determined to be at 0.00391 ppm CHO-MIF, the LOQ (limit of quantification) was defined as 10× standard deviation of the blank and was determined at 0.03125 ppm CHO-MIF (as marked by the black array in FIG. 4).

Figure 5:
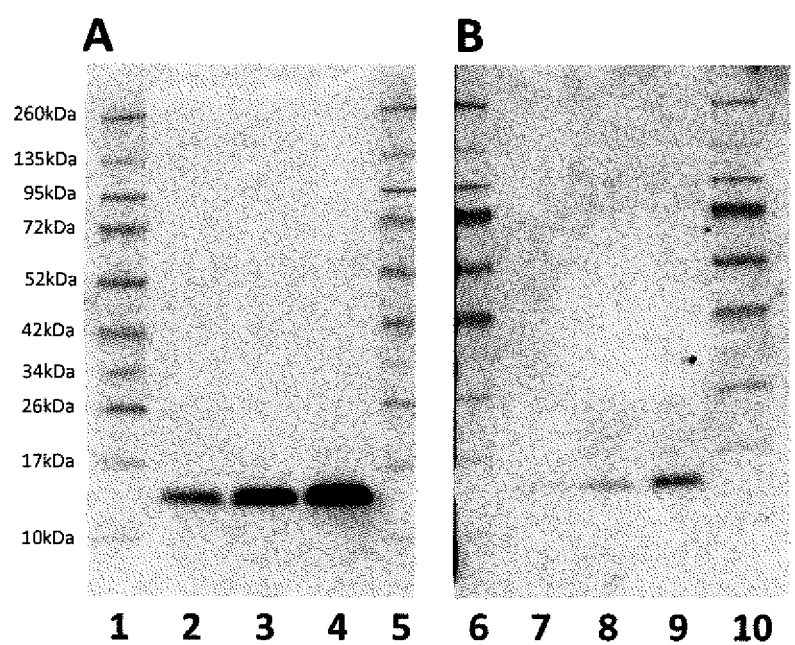

FIG. 5: Comparison polyclonal and inventive anti CHO-MIF antibody (WESTERN BLOT);

FIG. 5 shows two Western Blots with different amounts of recombinant CHO-MIF protein detected by the monoclonal rabbit anti CHO-MIF antibody A5 (FIG. 5A) and by a polyclonal rabbit anti CHO-MIF antibody, affinity purified against CHO-MIF (FIG. 5B), each at 5 µg/ml.

Lane 1, 5, 6 and 10 are molecular weight marker; lane 2 and 7: 2 ng CHO-MIF; lane 3 and 8: 1 ng CHO-MIF; lane 4 and 9: 0.5 ng CHO-MIF (i.e. Lane 1, 5, 6 and 10 are molecular weight marker; lane 2 and 7: 4 ppm CHO-MIF; lane 3 and 8: 2 ppm CHO-MIF; lane 4 and 9: 1 ppm CHO-MIF in the presence of 500 µg human anti (h)MIF antibodies.

Figure 6:
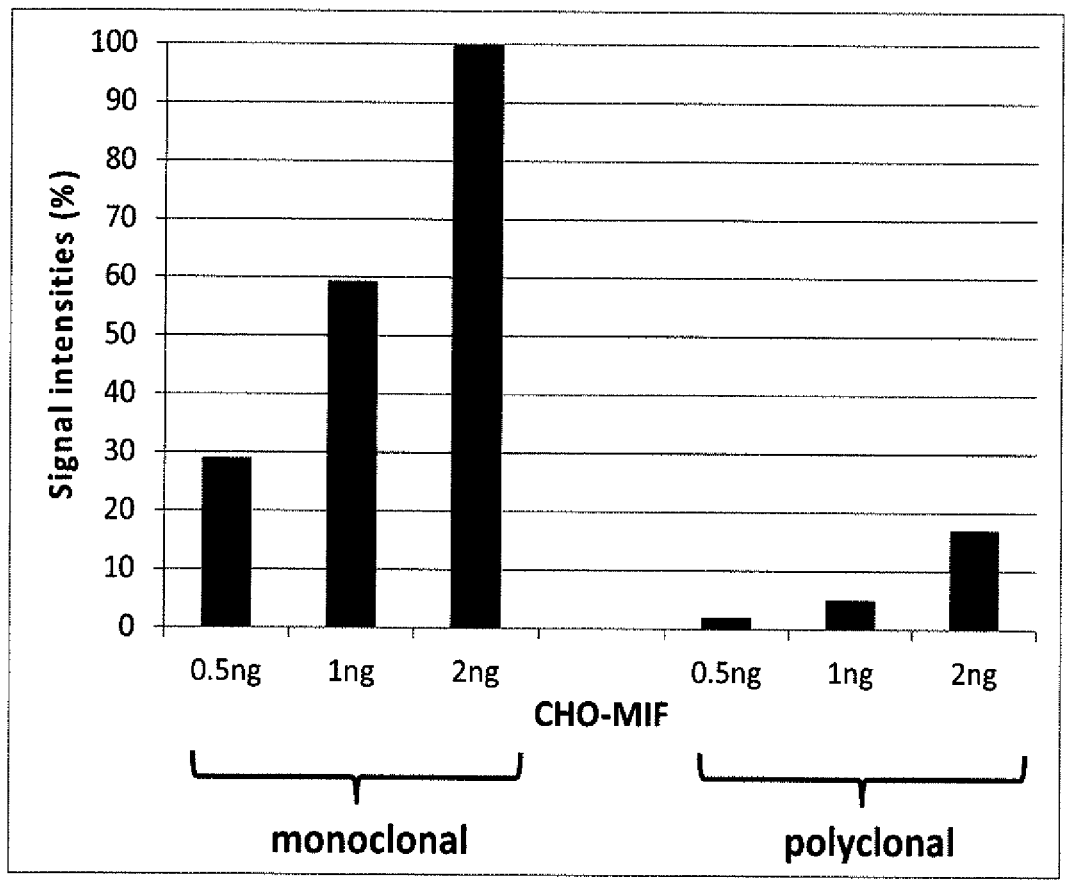

FIG. 6: Bar chart based on results of FIG. 5;

FIG. 6 is a bar chart of the CHO-MIF signals resultant from a Western Blot as shown in FIG. 5. The three bars from the left part are the corresponding signals from the monoclonal rabbit anti CHO-MIF antibody A5, the three bars on the right part are from the polyclonal rabbit anti CHO-MIF antibody. The signal from the 2 ng CHO-MIF (i.e. 4 ppm) detected by the monoclonal rabbit anti CHO-MIF antibody A5 was set to 100% and directly compared to the other CHO-MIF signals resultant from the scanner software.

The present inventors had also earlier succeeded in identifying and characterizing the CHO-MIF gene. On that basis they further succeeded in the provision of tools and methods allowing production and testing of anti-MIF antibody preparations in CHO cells, which preparations are essentially free of contaminating CHO-MIF. These tools and methods further allowed production and testing of all recombinant preparations as produced in CHO cells, which comprise recombinant CHO-MIF-binding protein, whereupon these preparations are essentially free of contaminating CHO-MIF. A recombinant CHO MIF binding protein in that context is a protein which binds to CHO MIF; thus, the protein binds to CHO MIF under immunoassay conditions, whereby a variety of immunoassay formats can be used to determine this binding, as is well known to a person skilled in the art. For example, solid phase ELISA immunoassays are routinely used to determine such binding reactions; see Harlow and Lane (1988), Antibodies, A Laboratory Manual, Col Spring harbour publications, New York, for a description of immunoassay formats and conditions that can be used.

This embodiment of the invention describes methods for the improvement of the sensitivity in the detection of CHO-MIF either as a free molecule or as bound to a potential drug such as an anti-(h)MIF antibody (e.g. RAM9). The detection of CHO-MIF in traces in final drug products is necessary because CHO-MIF is considered as an impurity of the process.

This invention describes a highly sensitive detection of CHO-MIF, preferably based on western blot technology or ELISA technology, using a monoclonal rabbit anti-MIF antibody which improves the detection sensitivity for CHO-MIF down to at least 0.0625 ppm by Western Blot and/or 0.03125 ppm by ELISA.

The ELISA assay is particularly preferred for this detection method as it allows an even lower detection limit for the CHO MIF contaminations.

The CHO-MIF protein and its detection by western blot technology was initially described in PCT/EP2012/069602. In this patent, the detection limit for CHO-MIF was described to be at 0.5 ppm using affinity purified polyclonal rabbit anti-CHO-MIF detection antibodies.

In the current invention the use of monoclonal rabbit anti-MIF antibodies which improve the detection sensitivity by Western blot down to 0.0625 ppm is described, which reflects an about ten-fold improvement in the detection limit as initially described in PCT/EP2012/069602.

The monoclonal antibody generation for this detection method is independent from animal resources, no immunization procedure is necessary. The new monoclonal rabbit anti-CHO-MIF antibody can be produced by a large scale production without the risk of batch to batch variation as encountered by polyclonal antibodies. The sequence of the preferred monoclonal rabbit anti-CHO-MIF antibody A5 has been elucidated by the inventors (see SEQ ID NO 17-20) and can theoretically also be transferred into an appropriate production expression system for high level production.

The present invention is directed to a highly sensitive method for the detection of ppm levels of CHO MIF contaminations, in particular CHO-MIF bound to anti-MIF antibodies in the presence of huge amounts (=500 µg/mL and even 20 mg/ml in the ELISA setup) of CHO-MIF free anti-MIF antibodies which during production in CHO cells of products, in particular antibodies and even more preferred anti-MIF antibodies or antigen-binding fragments thereof, can remain attached to the desired product in some cases. In a preferred embodiment, this detection method is based on the generation and purification of highly specific monoclonal anti CHO-MIF antibodies which are monoclonal antibodies, preferably rabbit antibodies.

With a detection method, as described in the present invention, which is able to detect CHO-MIF in very minor amounts in the presence of huge amounts of CHO-MIF free anti-MIF antibodies, it can be faithfully and reliably ensured that the final preparation is pure and in particular free of antigen/antibody complexes, e.g. CHO-MIF/anti-MIF complexes. Thereby, the present inventors succeeded in providing a recombinant product preparation, produced in CHO cells, comprising a product which would bind to CHO-MIF, in the event that CHO-MIF was present, wherein said preparation is essentially free of CHO-MIF. Preferably, the product as produced in the CHO cells is an antibody, more preferred an anti-MIF antibody, very preferred an anti human MIF antibody.

Preferred embodiments of these anti human MIF antibodies are described below and are designated as RAB4, RAB0, RAB9, RAM4, RAM0, and RAM9 respectively. These are internal designations. "RAB" designates an IgG4 antibody, "RAM" designates an IgG1 antibody.

The present invention thus provides a recombinant preparation, as defined above, which satisfies quality control requirements, in particular with regard to the essential absence of CHO-MIF contaminations.

The present inventors had already isolated mRNA coding for CHO-MIF as produced by CHO cells. The cDNA created by reverse transcription of this mRNA is cloned into a prokaryotic expression vector. The CHO-MIF protein expressed thereof in *E. coli* is purified to homogeneity.

Definitions and General Techniques

Unless otherwise defined herein, scientific and technical terms used in connection with the present invention shall have the meanings that are commonly understood by those of ordinary skill in the art, Generally, nomenclatures used in connection with, and techniques of, cell and tissue culture, molecular biology, immunology, microbiology, genetics and protein and nucleic acid chemistry described herein are those well known and commonly used in the art. The methods and techniques of the present invention are generally performed according to conventional methods well known in the art and as described in various general and more specific references that are cited and discussed throughout the present specification unless otherwise indicated, See, e.g., Sambrook et al., Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), which are incorporated herein by reference. "MIF" or "macrophage migration inhibitory factor" refers to the protein, which is known as a critical mediator in the immune and inflammatory response, especially as a counter-regulator of glucocorticoids. MIF includes mammalian MIF, specifically human MIF (Swiss-Prot primary accession number: P14174), wherein the monomeric form is encoded as a 115 amino acid protein but is produced as a 114 amino acid protein due to cleavage of the initial methionine. "MIF" also includes what was formerly known as "GIF" (glycosylation-inhibiting factor).

Also known are MIF derivatives/fragments, which exhibit functional or immunological properties of MIF, such as e.g. fragments or fusion proteins of MIF.

An "antibody" in this application refers to an intact antibody or an antigen-binding portion that competes with the intact antibody for specific binding. See generally, Fundamental Immunology, Ch. 7 (Paul, W., ed., 2nd ed. Raven Press, N.Y. (1989)) (incorporated by reference). The term antibody includes human antibodies, mammalian antibodies, isolated antibodies and genetically engineered forms such as, but not limited to, chimeric, camelized or humanized antibodies. The term "antibody" shall encompass throughout this application antigen-binding portions thereof as well.

The term "antigen-binding portion" of an antibody refers to one or more fragments of an antibody that retain the ability to specifically bind to an antigen (e.g. MIF). Antigen-binding portions may be produced by recombinant DNA techniques or by enzymatic or chemical cleavage of intact antibodies. Antigen-binding portions include Fab, Fab', F(ab')2, Fv, and complementarily determining regions (CDR) and fragments thereof, single-chain antibodies (scFv), chimeric antibodies, antibodies and polypeptides, that contain at least a portion of an antibody that is sufficient to confer specific antigen binding to the polypeptide. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia et al. J. Mol. Biol, 196:901-917 (1987), or Chothia et al., Nature 342:878-883 (1989). An antibody or antigen-binding portion thereof can be derivatized or linked to another functional molecule (e.g. another peptide or protein). For example, an antibody or antigen-binding portion thereof can be functionally linked to one or more other molecular entities, such as another antibody (e.g. a bispecific antibody or a diabody), a detectable agent, a cytotoxic agent, a pharmaceutical agent, and/or a linking molecule.

The term "human antibody" refers to any antibody in which the variable and constant domains are human sequences. The term encompasses antibodies with sequences derived from human genes, but which have been changed, e.g. to decrease possible immunogenicity, increase affinity, eliminate cysteines that might cause undesirable folding, etc. The term encompasses such antibodies produced recombinantly in non-human cells, which might impart glycosylation not typical of human cells.

The term "humanized antibody" refers to antibodies comprising human sequences and containing additionally non-human sequences.

The term "camelized antibody" refers to antibodies wherein the antibody structure or sequence has been changed to more closely resemble antibodies from camels, also designated camelid antibodies. Methods for the design and production of camelized antibodies are part of the general knowledge of a person skilled in the art.

The term "chimeric antibody" refers to an antibody that comprises regions from two or more different species. The term "isolated antibody" or "isolated antigen-binding portion thereof" refers to an antibody or an antigen-binding portion thereof that has been identified and selected from an antibody source such as a phage display library or a B-cell repertoire and has then been e.g. recombinantly prepared.

The term "polyclonal antibody" refers to a polyclonal antibody preparation, which may be a purified or partially purified polyclonal antibody fraction or which may be used in form of a crude serum from an animal immunized with the respective antigen, e.g. purified CHO-MIF.

The term "$K_D$" refers to the equilibrium dissociation constant of a Fab portion of a particular antibody with the respective antigen.

The term "vector" refers to a nucleic acid molecule capable of transporting another nucleic acid to which it has been linked. In some embodiments, the vector is a plasmid, i.e., a circular double stranded DNA loop into which additional DNA segments may be ligated.

The term "host cell" refers to a cell line, which is capable to produce a recombinant protein after introducing an expression vector. The term "recombinant cell line" refers to a cell line into which a recombinant expression vector has been introduced. It should be understood that "recombinant cell line" does not only mean the particular subject cell line but also the progeny of such a cell line. Because certain modifications may occur in succeeding generations due to either mutation or environmental influences, such progeny may not, in fact, be identical to the parent cell, but is still included within the scope of the term "recombinant cell line" as used herein. The host cell as preferably used according to the present invention is a CHO cell line.

The term "Western Blot" refers to the well-known and established technique of blotting proteins on a carrier membrane whereupon these proteins can subsequently be detected. The transfer to the membrane is carried out by well-known methods, of which diffusion, application of capillary forces or electrophoresis are examples, which however are by no means limiting the present method. In the case of an immunoblot, the detection is carried out by use of monoclonal or polyclonal antibodies. A "semi-quantitative" Western Blot in the context of the present invention means a Western Blot where the signal intensity from a sample (e.g.

CHO-MIF which can in some cases appear in complex with an anti-MIF antibody) is compared with the signal intensity from the corresponding standards (e.g. CHO-MIF). The signal can be e.g. a chemiluminescent signal quantified e.g. electronically by digital imaging systems.

Likewise, the present invention can be carried out by means of an ELISA technology, as is well known to the person of skill in the art, whereby the use of an ELISA assay is a preferred mode for the inventive detection method/quality control step.

The above mentioned antibodies are characterized and supported by both their sequences as well as by deposits as plasmids in *E. coli* (strain TG1), comprising either the light or the heavy chain of each of the above mentioned antibodies RAB0, RAB4 and RAB9, respectively and RAM0, RAM4 and RAM9, respectively. The plasmids are characterized by their DSM number which is the official number as obtained upon deposit under the Budapest Treaty with the German Collection of Microorganisms and Cell Cultures (DSMZ), Inhoffenstr. 7B, 38124, Braunschweig, Germany. The plasmids were deposited on 31.08.2011, in *E. coli* strains, respectively.

The plasmid with the DSM 25110 number comprises the light chain sequence of the anti-MIF antibody RAB4.

The plasmid with the DSM 25112 number comprises the heavy chain (IgG4) sequence of the anti-MIF antibody RAB4.

The co-expression of plasmids DSM 25110 and DSM 25112 in a suitable host cell results in the production of preferred anti-MIF antibody RAB4.

The plasmid with the DSM 25111 number comprises the light chain sequence of the anti-MIF antibody RAB9.

The plasmid with the DSM 25113 number comprises the heavy chain (IgG4) sequence of the anti-MIF antibody RAB9.

The co-expression of plasmids DSM 25111 and DSM 25113 in a suitable host cell results in the production of preferred anti-MIF antibody RAB9.

The plasmid with the DSM 25114 number comprises the light chain sequence of the anti-MIF antibody RAB0.

The plasmid with the DSM 25115 number comprises the heavy chain (IgG4) sequence of the anti-MIF antibody RAB0.

The co-expression of plasmids DSM 25114 and DSM 25115 in a suitable host cell, namely a CHO cell, results in the production of the preferred anti-MIF antibody RAB0.

Also deposited are antibodies RAM0, RAM9 and RAM4; all have been deposited with the DSMZ, Inhoffenstr. 7B, 38124, Braunschweig, Germany on Apr. 12, 2012 according to the Budapest Treaty, with the following designations:

RAM9—heavy chain: *E. coli* GA.662-01.pRAM9hc—DSM 25860.

RAM4—light chain: *E. coli* GA.906-04.pRAM4lc—DSM 25861.

RAM9—light chain: *E. coli* GA.661-01.pRAM9lc—DSM 25859.

RAM4—heavy chain: *E. coli* GA.657-02.pRAM4hc—DSM 25862.

RAM0—light chain: *E. coli* GA.906-01.pRAM0lc—DSM 25863.

RAM0—heavy chain: *E. coli* GA.784-01.pRAM0hc—DSM 25864.

The production of anti-(ox)MIF antibodies may also include any method known in the art for the cultivation of said transformed cells, e.g. in a continuous or batchwise manner, and the expression of the anti-(ox)MIF antibody, e.g. constitutive or upon induction. It is referred in particular to WO 2009/086920 for further reference for the production of anti-(ox)MIF antibodies. In a preferred embodiment, the anti-(ox)MIF antibodies as produced according to the present invention bind to oxMIF or an epitope thereof. Particularly preferred antibodies in accordance with the present invention are antibodies RAB9, RAB4 and/or RAB0 as well as RAM9, RAM4 and/or RAM0.

The sequences of these antibodies are partly also disclosed in WO 2009/086920; see in addition the sequence list of the present application and the following:

```
SEQ ID NO: 1 for the amino acid sequence of
the light chain of RAB9:
DIQMTQSPSS LSASVGDRVT ITCRSSQRIM TYLNWYQQKP

GKAPKLLIFV ASHSQSGVPS RFRGSGSETD FTLTISGLQP

EDSATYYCQQ SFWTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 2 for the amino acid sequence of
the light chain of RAB4:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 3 for the amino acid sequence of
the light chain of RAB0:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 4 for the amino acid sequence of
the light chain of RAB2:
DIQMTQSPVT LSLSPGERAT LSCRASQSVR SSYLAWYQQK

PGQTPRLLIY GASNRATGIP DRFSGSGSGT DFTLTISRLE

PEDFAVYYCQ QYGNSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 5 for the amino acid sequence of
the heavy chain of RAB9:
EVQLLESGGG LVQPGGSLRL SCAASGFTFS IYSMNWVRQA

PGKGLEWVSS IGSSGGTTYY ADSVKGRFTI SRDNSKNTLY

LQMNSLRAED TAVYYCAGSQ WLYGMDVWGQ GTTVTVSSAS

TKGPSVFPLA PCSRSTSEST AALGCLVKDY FPEPVTVSWN

SGALTSGVHT FPAVLQSSGL YSLSSVVTVP SSSLGTKTYT
```

CNVDHKPSNT KVDKRVESKY GPPCPPCPAP EFLGGPSVFL
FPPKPKDTLM ISRTPEVTCV VVDVSQEDPE VQFNWYVDGV
EVHNAKTKPR EEQFNSTYRV VSVLTVLHQD WLNGKEYKCK
VSNKGLPSSI EKTISKAKGQ PREPQVYTLP PSQEEMTKNQ
VSLTCLVKGF YPSDIAVEWE SNGQPENNYK TTPPVLDSDG
SFFLYSRLTV DKSRWQEGNV FSCSVMHEAL HNHYTQKSLS
LSLGK,

SEQ ID NO: 6 for the amino acid sequence of
the heavy chain of RAB4:
EVQLLESGGG LVQPGGSLRL SCAASGFTFS IYAMDWVRQA
PGKGLEWVSG IVPSGGFTKY ADSVKGRFTI SRDNSKNTLY
LQMNSLRAED TAVYYCARVN VIAVAGTGYY YYGMDVWGQG
TTVTVSSAST KGPSVFPLAP CSRSTSESTA ALGCLVKDYF
PEPVTVSWNS GALTSGVHTF PAVLQSSGLY SLSSVVTVPS
SSLGTKTYTC NVDHKPSNTK VDKRVESKYG PPCPPCPAPE
FLGGPSVFLF PPKPKDTLMI SRTPEVTCVV VDVSQEDPEV
QFNWYVDGVE VHNAKTKPRE EQFNSTYRVV SVLTVLHQDW
LNGKEYKCKV SNKGLPSSIE KTISKAKGQP REPQVYTLPP
SQEEMTKNQV SLTCLVKGFY PSDIAVEWES NGQPENNYKT
TPPVLDSDGS FFLYSRLTVD KSRWQEGNVF SCSVMHEALH
NHYTQKSLSL SLGK, SEQ ID NO: 7 for the amino acid sequence of
the heavy chain of RAB0:
EVQLLESGGG LVQPGGSLRL SCAASGFTFS WYAMDWVRQA
PGKGLEWVSG IYPSGGRTKY ADSVKGRFTI SRDNSKNTLY
LQMNSLRAED TAVYYCARVN VIAVAGTGYY YYGMDVWGQG
TTVTVSSAST KGPSVFPLAP CSRSTSESTA ALGCLVKDYF
PEPVTVSWNS GALTSGVHTF PAVLQSSGLY SLSSVVTVPS
SSLGTKTYTC NVDHKPSNTK VDKRVESKYG PPCPPCPAPE
FLGGPSVFLF PPKPKDTLMI SRTPEVTCVV VDVSQEDPEV
QFNWYVDGVE VHNAKTKPRE EQFNSTYRVV SVLTVLHQDW
LNGKEYKCKV SNKGLPSSIE KTISKAKGQP REPQVYTLPP
SQEEMTKNQV SLTCLVKGFY PSDIAVEWES NGQPENNYKT
TPPVLDSDGS FFLYSRLTVD KSRWQEGNVF SCSVMHEALH
NHYTQKSLSL SLGK, SEQ ID NO: 8 for the amino acid sequence of
the heavy chain of RAB2:
EVQLLESGGG LVQPGGSLRL SCAASGFTFS IYAMDWVRQA
PGKGLEWVSG IVPSGGFTKY ADSVKGRFTI SRDNSKNTLY
LQMNSLRAED TAVYYCARVN VIAVAGTGYY YYGMDVWGQG
TTVTVSSAST KGPSVFPLAP CSRSTSESTA ALGCLVKDYF
PEPVTVSWNS GALTSGVHTF PAVLQSSGLY SLSSVVTVPS
SSLGTKTYTC NVDHKPSNTK VDKRVESKYG PPCPPCPAPE
FLGGPSVFLF PPKPKDTLMI SRTPEVTCVV VDVSQEDPEV
QFNWYVDGVE VHNAKTKPRE EQFNSTYRVV SVLTVLHQDW
LNGKEYKCKV SNKGLPSSIE KTISKAKGQP REPQVYTLPP
SQEEMTKNQV SLTCLVKGFY PSDIAVEWES NGQPENNYKT
TPPVLDSDGS FFLYSRLTVD KSRWQEGNVF SCSVMHEALH
NHYTQKSLSL SLGK, SEQ ID NO: 9 for the amino acid sequence of
RAM0hc:
EVQLLESGGG LVQPGGSLRL SCAASGFTFS WYAMDWVRQA
PGKGLEWVSG IYPSGGRTKY ADSVKGRFTI SRDNSKNTLY
LQMNSLRAED TAVYYCARVN VIAVAGTGYY YYGMDVWGQG
TTVTVSSAST KGPSVFPLAP SSKSTSGGTA ALGCLVKDYF
PEPVTVSWNS GALTSGVHTF PAVLQSSGLY SLSSVVTVPS
SSLGTQTYIC NVNHKPSNTK VDKRVEPKSC DKTHTCPPCP
APELLGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLTCLVK GFYPSDIAVE WESNGQPENN
YKTTPPVLDS DGSFFLYSKL TVDKSRWQQG NVFSCSVMHE
ALHNHYTQKS LSLSPGK, SEQ ID NO: 10 for the amino acid sequence
of RAM01c:
DIQMTQSPGT LSLSPGERAT LSCRASQGVS SSSLAWYQQK
PGQAPRLLIY GTSSRATGIP DRFSGSASGT DFTLTISRLQ
PEDFAVYYCQ QYGRSLTFGG GTKVEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC, SEQ ID NO: 11 for the amino acid sequence
of RAM9hc:
EVQLLESGGG LVQPGGSLRL SCAASGFTFS IYSMNWVRQA
PGKGLEWVSS IGSSGGTTYY ADSVKGRFTI SRDNSKNTLY
LQMNSLRAED TAVYYCAGSQ WLYGMDVWGQ GTTVTVSSAS
TKGPSVFPLA PSSKSTSGGT AALGCLVKDY FPEPVTVSWN
SGALTSGVHT FPAVLQSSGL YSLSSVVTVP SSSLGTQTYI
CNVNHKPSNT KVDKRVEPKS CDKTHTCPPC PAPELLGGPS
VFLFPPKPKD TLMISRTPEV TCVVVDVSHE DPEVKFNWYV
DGVEVHNAKT KPREEQYNST YRVVSVLTVL HQDWLNGKEY
KCKVSNKALP APIEKTISKA KGQPREPQVY TLPPSREEMT
KNQVSLTCLV KGFYPSDIAV EWESNGQPEN NYKTTPPVLD
SDGSFFLYSK LTVDKSRWQQ GNVFSCSVMH EALHNHYTQK
SLSLSPGK, -continued

```
SEQ ID NO: 12 for the amino acid sequence
of RAM9lc:
DIQMTQSPSS LSASVGDRVT ITCRSSQRIM TYLNWYQQKP

GKAPKLLIFV ASHSQSGVPS RFRGSGSETD FTLTISGLQP

EDSATYYCQQ SFWTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 13 for the amino acid sequence
of RAM4hc:
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP SSKSTSGGTA ALGCLVKDYF

PEPVTVSWNS GALTSGVHTF PAVLQSSGLY SLSSVVTVPS

SSLGTQTYIC NVNHKPSNTK VDKRVEPKSC DKTHTCPPCP

APELLGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK,

SEQ ID NO: 14 for the amino acid sequence
of RAM4lc:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.
```

The further sequences as comprised in the enclosed sequence listing are the sequences of CHO MIF (SEQ ID NO:15, DNA; SEQ ID NO:16, protein) as well as the sequence of the inventive monoclonal rabbit antibody A5 (SEQ ID NO 17, heavy chain-DNA; and SEQ ID NO 18, heavy chain-protein; SEQ ID NO: 19, light chain-DNA and SEQ ID NO: 20, light chain-protein).

The anti-MIF antibody of the invention is preferably an isolated monoclonal antibody. The anti-MIF antibody can be an IgG, an IgM, an IgE, an IgA, or an IgD molecule. In other embodiments, the anti-MIF antibody is an IgG1, IgG2, IgG3 or IgG4 subclass. In other embodiments, the antibody is either subclass IgG1 or IgG4. In other embodiments, the antibody is subclass IgG4. In some embodiments, the IgG4 antibody has a single mutation changing the serine (serine228, according to the Kabat numbering scheme) to proline. Accordingly, the CPSC sub-sequence in the Fc region of IgG4 becomes CPPC, which is a sub-sequence in IgG1 (Angal et al. Mol Immunol 1993, 30, 105-108).

Additionally, the production of anti-(ox)MIF antibodies may include any method known in the art for the purification of an antibody, e.g. via anion exchange chromatography or affinity chromatography. In one embodiment the anti-(ox) MIF antibody can be purified from cell culture supernatants by size exclusion chromatography.

The terms "center region" and "C-terminal region" of MIF refer to the region of human MIF comprising amino acids 35-68 and aa 86-115, respectively, preferably aa 50-68 and aa 86 to 102 of human MIF, respectively. Particularly preferred antibodies of the present invention bind to either region aa 50-68 or region aa 86-102 of human MIF. This is also reflected by the binding of the preferred antibodies RAB0, RAB4 RAB2 and RAB9 as well as RAM4, RAM9 and RAM0 which bind as follows:

RAB4 and RAM4: aa 86-102
RAB9 and RAM9: aa 50-68
RAB0 and RAM0: aa 86-102
RAB2: aa 86-102

The term "epitope" includes any protein determinant capable of specific binding to an immunoglobulin or an antibody fragment. Epitopic determinants usually consist of chemically active surface groupings of molecules such as exposed amino acids, amino sugars, or other carbohydrate side chains and usually have specific three-dimensional structural characteristics, as well as specific charge characteristics.

The following description of the production of anti-(h) MIF antibodies shall illuminate exemplarily the process for producing a recombinant anti-(h)MIF antibody preparation which process includes a step for testing whether the purified antibody preparation is free from contaminating MIF, i.e. a detection step for CHO-MIF contaminations.

The production process according to the present invention of the anti-(h)MIF antibodies includes any method for the generation of recombinant DNA by genetic engineering, e.g. via reverse transcription of RNA and/or amplification of DNA and cloning into expression vectors. In some embodiments, the vector is a viral vector, wherein additional DNA segments may be ligated into the viral genome. In some embodiments, the vector is capable of autonomous replication in a host cell into which it is introduced (e.g. bacterial vectors having a bacterial origin of replication and episomal mammalian vectors). In other embodiments, the vector (e.g. non-episomal mammalian vectors) can be integrated into the genome of a host cell upon introduction into the host cell, and thereby replicated along with the host genome. Moreover, certain vectors are capable of directing the expression of genes to which they are operatively linked. Such vectors are referred to herein as "recombinant expression vectors" (or simply "expression vectors").

Anti-(h)MIF antibodies can be produced by means of conventional expression vectors, such as bacterial vectors (e.g. pBR322 and its derivatives), or eukaryotic vectors. Those sequences that encode the antibody can be provided with regulatory sequences that regulate the replication, expression and/or secretion from the host cell. These regulatory sequences comprise, for instance, promoters (e.g. CMV or SV40) and signal sequences. The expression vectors can also comprise selection and amplification markers, such as the dihydrofolate reductase gene (DHFR), hygromycin-B-phosphotransferase, and thymidine-kinase. The components of the vectors used, such as selection markers, replicons, enhancers, can either be commercially obtained or prepared by means of conventional methods. The vectors are here preferably constructed for the expression in cell cultures, namely in CHO cells.

The anti-(h)MIF antibody light chain gene and the anti-MIF antibody heavy chain gene can be inserted into separate vectors or both genes are inserted into the same expression vector. The antibody genes are inserted into the expression vector by standard methods, e.g. ligation of complementary restriction sites on the antibody gene fragment and vector, or blunt end ligation if no restriction sites are present.

The production of anti-(h)MIF antibodies or antigen-binding fragments thereof may include any method known in the art for the introduction of recombinant DNA into eukaryotic cells by transfection, e.g. via electroporation or microinjection. For example, the recombinant expression of anti-(h)MIF antibody can be achieved by introducing an expression plasmid containing the anti-(h)MIF antibody encoding DNA sequence under the control of one or more regulating sequences such as a strong promoter, into a CHO-cell line, by an appropriate transfection method resulting in cells having the introduced sequences stably integrated into the genome. The lipofection method is an example of a transfection method which may be used according to the present invention.

The production of anti-(h)MIF antibodies may also include any method known in the art for the cultivation of said transformed cells, e.g. in a continuous or batchwise manner, and the expression of the anti-(h)MIF antibody, e.g. constitutive or upon induction. It is referred in particular to WO 2009/086920 for further reference for the production of anti-(h)MIF antibodies. In a preferred embodiment, the antibodies of the CHO-MIF free anti-(h)MIF antibody preparation as produced according to the present invention bind to MIF or a MIF fragment. Particularly preferred antibodies to be produced in accordance with the present invention are RAB9, RAB4 and RAB0 (deposited as *E. coli* containing plasmids DSM 25114 and DSM 25115 for RAB0, DSM 25111 and DSM 25113 for RAB9 and DSM 25110 and DSM 25112 for RAB4, respectively).

The host cell type, which is used in the production method for the production of MIF, as described herein, is a CHO cell. In one embodiment, the anti-(h)MIF antibody is expressed in a DHFR-deficient CHO cell line, e.g. DXB11, and with the addition of G418 as a selection marker. When recombinant expression vectors encoding antibody genes are introduced into CHO host cells, the antibodies are produced by culturing the host cells for a period of time sufficient to allow for expression of the antibody in the host cells or secretion of the antibody into the culture medium in which the host cells are grown.

Anti-(h)MIF antibodies can be recovered from the culture medium using standard protein purification methods. The present invention now provides an advantageous method which clearly allows to improve and optimize the prior art methods for the production of anti-(h)MIF antibodies or antigen-binding fragments thereof.

In particular, the present inventors were the first to show that antibody preparations prepared with CHO cells could comprise CHO-MIF contaminations which would render the final preparation useless for pharmaceutical or research purposes.

The present inventors were then the first to identify and characterize the CHO-MIF gene (see SEQ ID NO: 15 and 16 of the enclosed sequence list). Based on this knowledge, the inventors here additionally provide a specific detection method which allows the detection of a CHO-MIF contamination bound to anti-(h)MIF antibodies, down to the low ppm range.

Very surprisingly, the present invention thus provides for the possibility of verifying that the production process for anti-(h)MIF antibodies, in particular the present purification process, is suitable for generating a preparation essentially free of CHO-MIF. This is the pre-requisite to establish a production method for the preparation of anti-(h)MIF antibodies free of CHO-MIF. In particular, this improvement allows the optimization and combination of methods known in the art for purification of the antibody preparations in a manner which depletes the CHO-MIF contaminants, thus allowing the provision of a highly pure final Ab-preparation, which is free of CHO-MIF contaminations. In addition, the inventive method is a highly sensitive detection method for said contaminations is a safeguard in the industrial production process, ensuring that a highly pure final Ab-preparation, which is free of CHO-MIF contaminations, is produced. Preferably, this detection is carried out with a detection step that uses a monoclonal rabbit anti-(h)MIF antibody that has been obtained by affinity purification against protein A. Affinity purification is carried out as well known to a person skilled in the art and described e.g. in Lottspeich F. and Zorbas H. (1998) Bioanalytik, Spektrum Akademischer Verlag Heidelberg-Berlin, ISBN 3-8274-0041-4.

The CHO-MIF contaminations can be detected down to ppm-level, in particular it is possible to detect CHO-MIF contaminations down to at least 0.0625 ppm using a highly sensitive monoclonal rabbit anti CHO-MIF antibody in a common Western Blot technology, exemplary quantified by a chemiluminescence signal in a digital quantitative imaging system (e.g. ImageQuant LAS 4000 from GE Healthcare) or down to 0.03125 ppm using an ELISA setup.

Thus, the term "essentially free of CHO MIF contaminations" in the context of this application shall mean a preparation, composition, formulation or product which has a content of less than 0.0625 ppm CHO MIF as detected by the present inventive Western Blot, or 0.03125 ppm as detected by the present inventive ELISA. "CHO-MIF contamination" in this context means CHO-MIF bound to a recombinantly produced product, e.g. to anti-(h)MIF antibodies in a preparation of a recombinantly produced product, e.g. anti-(h) MIF antibodies. A CHO MIF contamination can be a CHO MIF complex (with an anti-MIF antibody) or free soluble CHO MIF, or a mixture of both.

The high sensitivity of the present detection method is possible particularly with the monoclonal rabbit anti-MIF antibodies of this invention.

In a preferred embodiment, the above described detection method can be used for quality control of a protein produced recombinantly in a CHO MIF cell line, preferably an anti-MIF antibody production, in particular to ensure that the final preparation is essentially free of CHO MIF and CHO MIF complexes. The detection method can also be used for a quality control of CHO MIF knock out cell lines.

Preferred Embodiments

1. A method for the detection of CHO-MIF contaminations in a monoclonal anti-(h)MIF antibody preparation, comprising the step of contacting the anti-(h)MIF antibody preparation with a monoclonal rabbit anti-CHO-MIF antibody.

The step of "contacting the preparation with the monoclonal rabbit anti-CHO-MIF antibody" shall be understood broadly in the context of this application. It encompasses in its meaning both a direct contact between the preparation per se and the monoclonal rabbit anti-CHO-MIF antibody, as well as an indirect contact. The indirect contact could in one example be a contact which takes place after the preparation has been separated into components. This would exemplary be the case for a Western Blot, where the preparation is separated on a Blot and where the separated components are then brought into contact with the monoclonal rabbit anti-CHO-MIF antibody, or a contact as achieved by way of a common ELISA technology.

The term "anti-MIF antibody" and anti-(h)MIF antibody is used interchangeable herein and encompasses anti-MIF antibodies directed against human MIF, or MIF from other species, but preferably anti-MIF antibodies directed against human MIF (hMIF).

2. The method according to item 1 wherein the CHO-MIF contaminates a final CHO cell produced monoclonal anti-(h)MIF antibody—preparation or a preparation of antigen-binding portions thereof.
3. The method according to item 1 and/or 2 wherein the CHO-MIF is endogenous CHO-MIF produced by CHO cells, per se or CHO MIF complexed with the anti-(h)MIF antibody.
4. The method according to any one or more of items 1 to 3 wherein the detection step is carried out by a semi-quantitative Western Blot analysis, or by an ELISA, preferably a quantitative ELISA.
5. The method of any one or more items 1 to 4,
wherein said monoclonal antibody is the A5-antibody.
6. Use of a monoclonal rabbit anti-CHO-MIF antibody, preferably the A5-antibody, for the detection of CHO-MIF contaminations during production of monoclonal anti-MIF antibodies or antigen-binding fragments thereof or in the final preparation of monoclonal anti-(h)MIF antibody or antigen-binding portions thereof.
7. The use according to item 6 wherein the detection step is carried out as a semi-quantitative Western Blot analysis or as an ELISA, preferably a quantitative ELISA.
8. Essentially CHO MIF free anti-(h)MIF antibody preparation as obtainable by the method or use of items 1-7.
9. Recombinant anti-(h)MIF antibody preparation, produced in a CHO cell line, characterized in that said preparation is essentially free of CHO-MIF, wherein said preparation is produced by a method which comprises, preferably as a quality control step, the method of detection or the use of any one of the above items 1-8.
10. The anti-(h)MIF antibody preparation of any of items 8-9 above, which is essentially free of CHO MIF, or the method of any one or more of items 1-5, or the use of any of items 6 or 7, wherein the anti-(h)MIF antibody is selected from the group of RAB4, RAB0, RAB9, RAM4, RAM0 and/or RAM9.
11. The anti-(h)MIF antibody preparation, method or use of item 10, wherein the anti-(h)MIF antibody is RAM9.
12. A method for the production of an anti-(h)MIF antibody, preferably as defined in item 10, which comprises a detection method as defined in any one of items 1-5.
13. The method for the production of an anti-(h)MIF antibody of item 12, wherein the detection method is a quality control step for the verification that a CHO MIF content in the anti-(h)MIF antibody preparation is equal to or below 4 ppm.

EXAMPLES

Example 1

Establishment of a Highly Sensitive Western Blot for the Detection of CHO-MIF Using a Monoclonal Rabbit Anti CHO-MIF Antibody.

A) Immunization of Rabbits with Recombinant CHO-MIF (Full Length) or Synthesized Peptides of the Amino Acid Sequence of CHO-MIF.

3 months old New Zealand white rabbits were immunized using a standard protocol either of four injections with recombinant CHO-MIF or five injections with Keyhole Limpet Hemocyanin ligated peptides corresponding of the amino acid sequence of CHO-MIF. At the time of each injection, the antigen aliquot was thawed and combined with Complete Freund's Adjuvant (CFA) (for the first injection) or with incomplete Freund's Adjuvant (IFA) for the subsequently injections. The injection route was subcutaneous (SC). The immune response in rabbits was proved by the determination of the serum titer against full length CHO-MIF or peptides in a common ELISA procedure. After confirming the success of the immune response, the splenocytes were isolated by splenectomy about 4 days after the final boost.

B) Isolation of Lymphocytes

Spleens were taken from anesthetized rabbits (by injection of 60 mg/kg ketamine and 5 mg/kg xylazine via i.m.). The spleens were quickly excised without damaging and transferred in RPMI 1640 medium with 1% penicillin/streptomycin/fungizone (Fisher Cat # BW17745E; add 1:100 dilution) for washing (10 times using approx. 500 mL). After washing, each spleen was weighed and split into 2 g pieces and additionally washed in RPMI medium. The spleen pieces were punctured several (40-50) times with a 3 ml syringe needle (21 gauge) containing RPMI 1640 with 1% penicillin/streptomycin/fungizone while ballooning the spleen by injecting the medium to release the lymphocytes. Using a sterile plunger of a new 3 ml syringe the spleens were then crushed (in a Petri dish) into pieces and 10-15 mL fresh RPMI medium was added. For loosening the lymphocytes from the red blood cells the suspension was pipetted in and out using a common lab pipette. Afterwards, the crushed spleen was put through two 100 μm-cell strainers in a new 100 mm dish. The flow through containing the cells was being placed in a 50 ml tube; debris remains on the strainers. Remaining spleen from each strainer was taken back into the dish. The harvesting was repeated two more times, with a final flow through volume of 50 ml RPMI.

The flow through from the harvesting step was spun down for 5-10 min at 450×g, the supernatant was discarded. To the red pellet Cell Lysis Buffer was added and incubated at least for 4 min. Then RPMI medium was applied to bring the total volume up to 50 mL. The cells were again spun down for 5-10 min at 450×g, the supernatant was aspirated and discarded. The cell pellet was washed one more time and the remaining cells resuspended and filled up to 50 mg again with RPMI medium. After a final spinning down for 5-10 min at 450×g, the supernatant was again removed and the cell pellet resuspended with 20 mL of RPMI medium. Afterwards, cells were counted and the viability determined (80-90%).

C) Fusion Process to Generate Hybridoma Cells

About 200 millions of lymphocytes were fused with an adequate amount of fusion partner cells and plated on 10 (or 20) 96 well plates. The plates were kept in tissue culture incubators under standard conditions. Cell growth and fusion efficiency were monitored and supernatant from positive wells was tested for reactivity (multiclone level), The best multiclones concerning their antibody production and viability were isolated and subcloned by dilution D) Production of Monoclonal Rabbit Antibodies The particularly suitable subclone A5 was cultivated in cellflasks including RPMI-1640 medium with 10% inactivated FCS (fetal calf serum), rabbit hybridoma Supplement A; Glutamax-I (100×); 55 µM 2-Mercaptoethanol and Penicillin/Streptomycin (10 000 units/ml). Cultivation was done with 5% $CO_2$ at 37° C. Cells were diluted to $3*10^5$ cells every third day. All the supernatants were collected, pooled and used for the purification of monoclonal rabbit antibodies.

E) Purification of Monoclonal Rabbit Antibodies

The complete cell culture supernatant was diluted 1:1 with 20 mM $Na_2HPO_4$ buffer, pH 7.2 and applied to a 5 mL protein A column (Mab Select Sure, GE Healthcare). After washing with 10 column volumes with the 20 mM $Na_2HPO_4$ the elution was done with 100 mM glycine buffer, pH 2.8. The elution peak was re-buffered in PBS (phosphate buffered saline), pH 7.2 by commercial desalting column (GE Healthcare).

The final monoclonal rabbit anti CHO-MIF antibodies A5 were stored in aliquots at −80° C. (see also SEQ ID NO 17 and 18).

F) Western Blot Procedure Using Monoclonal Rabbit Anti CHO-MIF Antibodies

Antibody samples of interest were separated by SDS-PAGE electrophoresis (sodium dodecyl sulphate-polyacrylamide-gel electrophoresis) and transferred to a commonly used membrane e.g. polyvinylidene fluoride (PVDF) or nitrocellulose. The target protein CHO-MIF was identified and quantified by the specific monoclonal rabbit anti CHO-MIF antibody and chemiluminescence reaction using a corresponding secondary antibody conjugate.

Samples were diluted 1:1 in SDS buffer (100 mM Tris, 4% SDS, 0.2% bromophenol blue, 20% glycerin, 200 mM DTT, pH 6.8) and incubated for 5 minutes at 99° C. (protein reduction and denaturation step). Afterwards, a defined concentration of each sample was loaded on a 4-12% Bis/Tris Gel (Invitrogen) and separated by gel electrophoresis with subsequent electrotransfer using an iBlot system (Invitrogen) to a suitable membrane (e.g. PVDF). After that the blot membrane was transferred into a snap holder (Millipore). For the reduction of unspecific binding effects the membrane was blocked by 0.5% dry milk diluted in TBST buffer (25 mM Tris, 150 mM NaCl, 0.1% polysorbate 20, pH 7.5). 3.5 µg/mL of the monoclonal rabbit anti CHO-MIF antibody, diluted in TBST was applied and incubated for 10 minutes at room temperature. Removal of unbound proteins was achieved by washing steps with TBST. A secondary antibody conjugated with horseradish peroxides (e.g. donkey anti rabbit/HRP) was incubated with the membrane for 10 minutes at RT and washed again with TBST. The specific CHO-MIF signal was detected and quantified by addition of a chemiluminescence substrate (e.g. Super Signal West Femto, Pierce) using a Luminescent Image Analyzer from Fujifilm (LAS-4000) (See also FIG. 1).

ELISA Procedure Using Monoclonal Rabbit Anti CHO-MIF Antibodies

To demonstrate the sensitivity of the monoclonal rabbit anti CHO-MIF antibody A5 in an ELISA setup, samples including different contents of CHO-MIF were spiked each with 20 mg/mL anti (h)MIF antibody (RAM9) and applied to a microtiter plate coated with rabbit anti CHO-MIF antibody A6 (40 µg/ml in 50 mM sodium carbonate buffer). After an incubation step for 1 h at 30° C., unbound material was washed out by 4 washing steps (with PBS). A biotin labeled monoclonal rabbit anti CHO-MIF antibody A5 was applied and incubated for 30 min at 30° C. After additional washing steps HRP labeled streptavidin was applied to bind specifically to the biotin labeled rabbit anti CHO-MIF A5 antibody. Within the next 30 minutes incubation at 30° C. the complex was colorized by a HRP substrate (3,3',5,5'-Tetramethylbenzidine). Finally, the reaction was stopped by adding 1.8 M H2SO4 and the change of the color was analyzed by a common ELISA reader at 450 nm.

The above procedure is only exemplary. The person of skill in the art is well aware how to carry out an ELISA procedure, using the inventive monoclonal antibody, preferably the anti CHO-MIF A5 antibody.

Monoclonal Antibody Sequence

The DNA and amino acid sequence of the monoclonal rabbit antibody is shown in the following:

```
A5 (heavy chain of inventive antibody;
SEQ ID NO: 17)
ATGGAGACTG GGCTGCGCTG GCTTCTCCTG GTCGCTGTGC

TCAAAGGTGT CCAGTGTCAG TCGGTGGAGG AGTCCGGGGG

TCGCCTGGTC ACGCCTGGGA CACCCCTGAC ACTCACCTGC

ACAGTGTCTG GATTCTCCCT CGGCAGCTAC GACATGAGCT

GGGTCCGCCA GGCTCCAGGG AAGGGACTGG AATGGATCGG

AGTGATTTTT ACTGATGATA ACACATACTA CGCGAGCTGG

GCGAAAGGCC GATTCACCAT CTCCAAAGCC TCGTCGACCA

CGGTGGATCT GAAAATCACC AGTCCGACAA CCGAGGACAC

GGCCACCTAC TTCTGTTCCA AATTTGGTTC TGTCGGTGAC

TTGTGGGGCC CAGGCACCCT GGTCACCGTC TCCTCAGGGC

AACCTAAGGC TCCATCAGTC TTCCCACTGG CCCCCTGCTG

CGGGGACACA CCCAGCTCCA CGGTGACCCT GGGCTGCCTG

GTCAAAGGCT ACCTCCCGGA GCCAGTGACC GTGACCTGGA

ACTCGGGCAC CCTCACCAAT GGGGTACGCA CCTTCCCGTC

CGTCCGGCAG TCCTCAGGCC TCTACTCGCT GAGCAGCGTG

GTGAGCGTGA CCTCAAGCAG CCAGCCCGTC ACCTGCAACG

TGGCCCACCC AGCCACCAAC ACCAAAGTGG ACAAGACCGT

TGCGCCCTCG ACATGCAGCA AGCCCACGTG CCCACCCCCT

GAACTCCTGG GGGGACCGTC TGTCTTCATC TTCCCCCCAA

AACCCAAGGA CACCCTCATG ATCTCACGCA CCCCCGAGGT
```

-continued

```
CACATGCGTG GTGGTGGACG TGAGCCAGGA TGACCCCGAG

GTGCAGTTCA CATGGTACAT AAACAACGAG CAGGTGCGCA

CCGCCCGGCC GCCGCTACGG GAGCAGCAGT TCAACAGCAC

GATCCGCGTG GTCAGCACCC TCCCCATCGC GCACCAGGAC

TGGCTGAGGG GCAAGGAGTT CAAGTGCAAA GTCCACAACA

AGGCACTCCC GGCCCCCATC GAGAAAACCA TCTCCAAAGC

CAGAGGGCAG CCCCTGGAGC CGAAGGTCTA CACCATGGGC

CCTCCCCGGG AGGAGCTGAG CAGCAGGTCG GTCAGCCTGA

CCTGCATGAT CAACGGCTTC TACCCTTCCG ACATCTCGGT

GGAGTGGGAG AAGAACGGGA AGGCAGAGGA CAACTACAAG

ACCACGCCGG CCGTGCTGGA CAGCGACGGC TCCTACTTCC

TCTACAGCAA GCTCTCAGTG CCCACGAGTG AGTGGCAGCG

GGGCGACGTC TTCACCTGCT CCGTGATGCA CGAGGCCTTG

CACAACCACT ACACGCAGAA GTCCATCTCC CGCTCTCCGG

GTAAATGA
```

A5 (heavy chain of inventive antibody,
SEQ ID NO: 18)
```
METGLRWLLL VAVLKGVQCQ SVEESGGRLV TPGTPLTLTC

TVSGFSLGSY DMSWVRQAPG KGLEWIGVIF TDDNTYYASW

AKGRFTISKA SSTTVDLKIT SPTTEDTATY FCSKFGSVGD

LWGPGTLVTV SSGQPKAPSV FPLAPCCGDT PSSTVTLGCL

VKGYLPEPVT VTWNSGTLTN GVRTFPSVRQ SSGLYSLSSV

VSVTSSSQPV TCNVAHPATN TKVDKTVAPS TCSKPTCPPP

ELLGGPSVFI FPPKPKDTLM ISRTPEVTCV VVDVSQDDPE

VQFTWYINNE QVRTARPPLR EQQFNSTIRV VSTLPIAHQD

WLRGKEFKCK VHNKALPAPI EKTISKARGQ PLEPKVYTMG

PPREELSSRS VSLTCMINGF YPSDISVEWE KNGKAEDNYK

TTPAVLDSDG SYFLYSKLSV PTSEWQRGDV FTCSVMHEAL

HNHYTQKSIS RSPGK.
```

A5 (light chain of inventive antibody;
SEQ ID NO: 19)
```
ATGGACACGA GGGCCCCCAC TCAGCTGCTG GGGCTCCTGC

TGCTCTGGCT CCCAGGTGCC ACATTTGCTC AAGTGCTGAC

CCAGACTCCA TCCTCCGTGT CTGCCGCTGT GGGAGGCACA

GTCACCATCA ACTGCCAGTC CAGTCAGAGT GTTTATGGTG

GCAACTACTT ATCCTGGTAT CAGCAGAAAC CAGGGCAGCC

TCCCAAGCTC CTGATCTATG CTGCATCCAC TCTGGCATCT

GGGGTCCCAT CGCGGTTCAA AGGCAGTGGA TCTGGGACAC

AGTTCACTCT CACAATCGCC GAAGTACAGT GTGACGATGC

TGCCACTTAC TACTGTCAAG GGTATTTTTA TGGTGTTATT

AATAGTTTCG GCGGAGGGAC CGAGGTGGTG GTCAAAGGTG

ATCCAGTTGC ACCTACTGTC CTCATCTTCC CACCAGCTGC

TGATCAGGTG GCAACTGGAA CAGTCACCAT CGTGTGTGTG

GCGAATAAAT ACTTTCCCGA TGTCACCGTC ACCTGGGAGG

TGGATGGCAC CACCCAAACA ACTGGCATCG AGAACAGTAA

AACACCGCAG AATTCTGCAG ATTGTACCTA CAACCTCAGC

AGCACTCTGA CACTGACCAG CACACAGTAC AACAGCCACA

AAGAGTACAC CTGCAAGGTG ACCCAGGGCA CGACCTCAGT

CGTCCAGAGC TTCAATAGGG GTGACTGTTA G
```

A5 (light chain of inventive antibody;
SEQ ID NO: 20)
```
MDTRAPTQLL GLLLLWLPGA TFAQVLTQTP SSVSAAVGGT

VTINCQSSQS VYGGNYLSWY QQKPGQPPKL LIYAASTLAS

GVPSRFKGSG SGTQFTLTIA EVQCDDAATY YCQGYFYGVI

NSFGGGTEVV VKGDPVAPTV LIFPPAADQV ATGTVTIVCV

ANKYFPDVTV TWEVDGTTQT TGIENSKTPQ NSADCTYNLS

STLTLTSTQY NSHKEYTCKV TQGTTSVVQS FNRGDC
```

The epitope mapping is further shown in FIGS. 2 and 3 and the description thereof.

Example 2: Determination of LOD and LOQ

Monoclonal rabbit anti CHO-MIF antibody A6, which binds to a different CHO-MIF epitope than rabbit anti CHO-MIF antibody A5, was coated on an microtiter plate for capturing free soluble CHO-MIF or in complex with the anti-(h)MIF antibody. After a blocking step for the reduction of unspecific bindings samples and standards were applied and incubated.

Unbound material was washed out and CHO-MIF (solitary or in complex with an anti-(h)MIF antibodies) was detected by the biotin labeled monoclonal rabbit anti CHO-MIF antibody A5. HRP labeled streptavidin was finally applied to bind specifically to the biotin labeled rabbit anti CHO-MIF A5 antibody. The complex was finally identified by a colour change of the HRP substrate and quantified at 450 nm in a common ELISA reader against the reference standards.

The results are shown in FIG. 4. The limit of detection was determined at 0.00391 ppm CHO-MIF, while the LOQ was at 0.03125 ppm CHO-MIF (in the presence of 20 mg/ml anti-human MIF antibody).

Example 3: Comparison of the Inventive Antibody to a Polyclonal Rabbit Anti-CHO MIF Antibody The polyclonal rabbit antibodies in the following examples were detected by a commercial available horse radish peroxidase (HRP) conjugated donkey anti rabbit IgG in combination with a commercial HRP substrate. The resultant western blots were scanned by a LAS4000 Image Reader and the CHO-MIF signals quantified by the Image Quant LAS4000 software.

The Western Blots demonstrate the increased and advantageous sensitivity by using the monoclonal rabbit anti CHO-MIF antibody A5 compared to CHO-MIF (also affinity purified) polyclonal rabbit anti CHO MIF antibody.

Lane 1, 5, 6 and 10 are molecular weight marker; lane 2 and 7: 0.5 ng CHO-MIF; lane 3 and 8: 1 ng CHO-MIF; lane 4 and 9: 2 ng CHO-MIF. This corresponds to the following ppm values: Lane 1, 5, 6 and 10 are molecular weight marker; lane 2 and 7: 4 ppm CHO-MIF; lane 3 and 8: 2 ppm CHO-MIF; lane 4 and 9: 1 ppm CHO-MIF in the presence of 500 μg human anti MIF antibodies.

The results are further shown in the bar chart of FIG. 6.

These Western Blots demonstrate the advantageous sensitivity by using the monoclonal rabbit anti CHO-MIF antibody A5 compared to an affinity purified polyclonal rabbit anti CHO-MIF antibody. Using the same procedure and the same antibody concentrations for detecting CHO-MIF, the highest CHO-MIF signals were detected by the monoclonal antibody A5 as shown in FIG. 5 A.

As has been shown in the earlier examples, the monoclonal anti CHO_MIF antibodies provide a sensitivity which is even further improved and are thus an advantageous contribution to the prior art.

Indeed, the present monoclonal antibodies are not only improved regarding their sensitivity but are the only available antibodies which are capable to detecting trace amounts of CHO MIF in an anti-MIF antibody preparation below the limit of 4 ppm. This ppm-limit is the currently prerequisite highest limit of CHO MIF contaminations considered allowable in anti-MIF antibody preparations. The presently claimed monoclonal anti-CHO MIF antibodies are thus an advantageous means to verify that the CHO MIF contaminations are below the acceptable limit. In particular, a quantitative ELISA is suitable to confirm that the value for the limit for CHO MIF contaminations in an anti-(h) MIF antibody preparation is fulfilled.

---

The invention claimed is:

1. A method for the detection of Chinese hamster ovary (CHO)-migration inhibitory factor (MIF) contaminations in a monoclonal anti-(h)MIF antibody preparation, comprising contacting the anti-(h)MIF antibody preparation with a monoclonal rabbit anti-CHO-MIF antibody, and detecting CHO-MIF contaminations, wherein the monoclonal rabbit anti-CHO-MIF antibody is an A5 antibody, wherein the A5 antibody comprises a heavy chain characterized by SEQ ID NO: 18 and a light chain characterized by SEQ ID NO: 20.

2. The method according to claim 1 wherein the CHO-MIF contaminates a final CHO cell produced monoclonal anti-(h)MIF antibody-preparation or a preparation of antigen-binding portions thereof.

3. The method according to claim 1 wherein the CHO-MIF is endogenous CHO-MIF produced by CHO cells, per se or CHO MIF complexed with the anti-(h)MIF antibody.

4. The method according to claim 1 wherein the detection step is carried out by a semi-quantitative Western Blot analysis, or by an ELISA.

5. The method according to claim 4 wherein the ELISA is a quantitative ELISA.

6. A method for the detection of CHO-MIF contaminations in a preparation during production of monoclonal anti-(h)MIF antibodies or antigen-binding fragments thereof or in the final preparation of monoclonal anti-(h)MIF antibody or antigen-binding portions thereof, the method comprising:
   i) contacting the monoclonal anti-(h)MIF antibodies or antigen-binding fragments thereof containing preparation with a monoclonal rabbit anti-CHO-MIF antibody, and
   ii) detecting the presence of CHO-MIF contaminations in the preparation,
   wherein the monoclonal rabbit anti-CHO-MIF antibody is an A5 antibody, wherein the A5 antibody comprises a heavy chain characterized by SEQ ID NO: 18 and a light chain characterized by of SEQ ID NO: 20.

7. The method according to claim 6 wherein the detection step is carried out as a semi-quantitative Western Blot analysis or as an ELISA.

8. The method according to claim 7 wherein the ELISA is a quantitative ELISA.

9. The method according to claim 1 wherein the anti-(h) MIF antibody is selected from the group consisting of RAB4, RAB0, RAB9, RAM4, RAM0 and RAM9, wherein
   RAB4 comprises a light chain characterized by SEQ ID NO: 2, and a heavy chain characterized by SEQ ID NO: 6;
   RAM4 comprises a light chain characterized by SEQ ID NO: 14, and a heavy chain characterized by SEQ ID NO: 13;
   RAB9 comprises a light chain characterized by SEQ ID NO: 1, and a heavy chain characterized by SEQ ID NO: 5;
   RAM9 comprises a light chain characterized by SEQ ID NO: 12, and a heavy chain characterized by SEQ ID NO: 11;
   RAB0 comprises a light chain characterized by SEQ ID NO: 3, and a heavy chain characterized by SEQ ID NO: 7; and
   RAM0 comprises a light chain characterized by SEQ ID NO: 10, and a heavy chain characterized by SEQ ID NO: 9.

10. The method according to claim 9 wherein the anti-(h)MIF antibody is RAM9, which comprises a light chain characterized by SEQ ID NO: 12, and a heavy chain characterized by SEQ ID NO: 11.

11. The method according to claim 6 wherein the anti-(h)MIF antibody is selected from the group consisting of RAB4, RAB0, RAB9, RAM4, RAM0 and RAM9, wherein RAB4 comprises a light chain characterized by SEQ ID NO: 2, and a heavy chain characterized by SEQ ID NO: 6;

RAM4 comprises a light chain characterized by SEQ ID NO: 14, and a heavy chain characterized by SEQ ID NO: 13;

RAB9 comprises a light chain characterized by SEQ ID NO: 1, and a heavy chain characterized by SEQ ID NO: 5;

RAM9 comprises a light chain characterized by SEQ ID NO: 12, and a heavy chain characterized by SEQ ID NO: 11;

RAB0 comprises a light chain characterized by SEQ ID NO: 3, and a heavy chain characterized by SEQ ID NO: 7; and RAM0 comprises a light chain characterized by SEQ ID NO: 10, and a heavy chain characterized by SEQ ID NO: 9.

12. The method according to claim 11 wherein the anti-(h)MIF antibody is RAM9, which comprises a light chain characterized by SEQ ID NO: 12, and a heavy chain characterized by SEQ ID NO: 11.

* * * * *

SEQUENCE LISTING

<160> NUMBER OF SEQ ID NOS: 20

<210> SEQ ID NO 1
<211> LENGTH: 214
<212> TYPE: PRT
<213> ORGANISM: Artificial Sequence
<220> FEATURE:
<223> OTHER INFORMATION: Light chain of RAB9

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 2
<211> LENGTH: 214
<212> TYPE: PRT

<213> ORGANISM: Artificial Sequence
<220> FEATURE:
<223> OTHER INFORMATION: Light chain of RAB4

<400> SEQUENCE: 2

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 3
<211> LENGTH: 214
<212> TYPE: PRT
<213> ORGANISM: Artificial Sequence
<220> FEATURE:
<223> OTHER INFORMATION: Light chain of RAB0

<400> SEQUENCE: 3

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 214
<212> TYPE: PRT
<213> ORGANISM: Artificial Sequence
<220> FEATURE:
<223> OTHER INFORMATION: Light chain of RAB2

<400> SEQUENCE: 4

Asp Ile Gln Met Thr Gln Ser Pro Val Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Thr Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 445
<212> TYPE: PRT
<213> ORGANISM: Artificial Sequence
<220> FEATURE:
```

<223> OTHER INFORMATION: Heavy chain of RAB9

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Ser Ile Gly Ser Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Gln Trp Leu Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

-continued

```
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 6
<211> LENGTH: 454
<212> TYPE: PRT
<213> ORGANISM: Artificial Sequence
<220> FEATURE:
<223> OTHER INFORMATION: Heavy chain of RAB4

<400> SEQUENCE: 6

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ile Tyr
            20                  25                  30
Ala Met Asp Trp Val Arg Gln Ala Pro Gly Lys Gly Leu Glu Trp Val
        35                  40                  45
Ser Gly Ile Val Pro Ser Gly Gly Phe Thr Lys Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Asn Val Ile Ala Val Ala Gly Thr Gly Tyr Tyr Tyr Tyr
            100                 105                 110
Gly Met Asp Val Trp Gly Gln Gly Thr Thr Val Thr Val Ser Ser Ala
        115                 120                 125
Ser Thr Lys Gly Pro Ser Val Phe Pro Leu Ala Pro Cys Ser Arg Ser
    130                 135                 140
Thr Ser Glu Ser Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
            180                 185                 190
Ser Ser Val Val Thr Val Pro Ser Ser Ser Leu Gly Thr Lys Thr Tyr
        195                 200                 205
Thr Cys Asn Val Asp His Lys Pro Ser Asn Thr Lys Val Asp Lys Arg
    210                 215                 220
Val Glu Ser Lys Tyr Gly Pro Pro Cys Pro Pro Cys Pro Ala Pro Glu
225                 230                 235                 240
Phe Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser Gln Glu Asp Pro Glu Val Gln Phe Asn Trp Tyr Val Asp Gly
        275                 280                 285
Val Glu Val His Asn Ala Lys Thr Lys Pro Arg Glu Glu Gln Phe Asn
    290                 295                 300
Ser Thr Tyr Arg Val Val Ser Val Leu Thr Val Leu His Gln Asp Trp
305                 310                 315                 320
```

-continued

```
Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
        340                 345                 350

Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450
```

<210> SEQ ID NO 7
<211> LENGTH: 454
<212> TYPE: PRT
<213> ORGANISM: Artificial Sequence
<220> FEATURE:
<223> OTHER INFORMATION: Heavy chain of RAB0

<400> SEQUENCE: 7

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ala Met Asp Trp Val Arg Gln Ala Pro Gly Lys Gly Leu Glu Trp Val
        35                  40                  45

Ser Gly Ile Tyr Pro Ser Gly Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220
```

```
Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
            325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
            405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
        450

<210> SEQ ID NO 8
<211> LENGTH: 454
<212> TYPE: PRT
<213> ORGANISM: Artificial Sequence
<220> FEATURE:
<223> OTHER INFORMATION: Heavy chain of RAB2

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125
```

```
Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 9
<211> LENGTH: 457
<212> TYPE: PRT
<213> ORGANISM: Artificial Sequence
<220> FEATURE:
<223> OTHER INFORMATION: RAM0hc

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30
```

```
Ala Met Asp Trp Val Arg Gln Ala Pro Gly Lys Gly Leu Glu Trp Val
         35                  40                  45
Ser Gly Ile Tyr Pro Ser Gly Gly Arg Thr Lys Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
             85                  90                  95
Ala Arg Val Asn Val Ile Ala Val Gly Thr Gly Tyr Tyr Tyr Tyr Tyr
             100                 105                 110
Gly Met Asp Val Trp Gly Gln Gly Thr Thr Val Thr Val Ser Ser Ala
             115                 120                 125
Ser Thr Lys Gly Pro Ser Val Phe Pro Leu Ala Pro Ser Ser Lys Ser
 130                 135                 140
Thr Ser Gly Gly Thr Ala Ala Leu Gly Cys Leu Val Lys Asp Tyr Phe
 145                 150                 155                 160
Pro Glu Pro Val Thr Val Ser Trp Asn Ser Gly Ala Leu Thr Ser Gly
             165                 170                 175
Val His Thr Phe Pro Ala Val Leu Gln Ser Ser Gly Leu Tyr Ser Leu
             180                 185                 190
Ser Ser Val Val Thr Val Pro Ser Ser Ser Leu Gly Thr Gln Thr Tyr
             195                 200                 205
Ile Cys Asn Val Asn His Lys Pro Ser Asn Thr Lys Val Asp Lys Arg
             210                 215                 220
Val Glu Pro Lys Ser Cys Asp Lys Thr His Thr Cys Pro Pro Cys Pro
 225                 230                 235                 240
Ala Pro Glu Leu Leu Gly Gly Pro Ser Val Phe Leu Phe Pro Pro Lys
             245                 250                 255
Pro Lys Asp Thr Leu Met Ile Ser Arg Thr Pro Glu Val Thr Cys Val
             260                 265                 270
Val Val Asp Val Ser His Glu Asp Pro Glu Val Lys Phe Asn Trp Tyr
             275                 280                 285
Val Asp Gly Val Glu Val His Asn Ala Lys Thr Lys Pro Arg Glu Glu
 290                 295                 300
Gln Tyr Asn Ser Thr Tyr Arg Val Val Ser Val Leu Thr Val Leu His
 305                 310                 315                 320
Gln Asp Trp Leu Asn Gly Lys Glu Tyr Lys Cys Lys Val Ser Asn Lys
             325                 330                 335
Ala Leu Pro Ala Pro Ile Glu Lys Thr Ile Ser Lys Ala Lys Gly Gln
             340                 345                 350
Pro Arg Glu Pro Gln Val Tyr Thr Leu Pro Pro Ser Arg Glu Glu Met
             355                 360                 365
Thr Lys Asn Gln Val Ser Leu Thr Cys Leu Val Lys Gly Phe Tyr Pro
 370                 375                 380
Ser Asp Ile Ala Val Glu Trp Glu Ser Asn Gly Gln Pro Glu Asn Asn
 385                 390                 395                 400
Tyr Lys Thr Thr Pro Pro Val Leu Asp Ser Asp Gly Ser Phe Phe Leu
             405                 410                 415
Tyr Ser Lys Leu Thr Val Asp Lys Ser Arg Trp Gln Gln Gly Asn Val
             420                 425                 430
Phe Ser Cys Ser Val Met His Glu Ala Leu His Asn His Tyr Thr Gln
             435                 440                 445
Lys Ser Leu Ser Leu Ser Pro Gly Lys
```

-continued

```
        450                 455
```

<210> SEQ ID NO 10
<211> LENGTH: 214
<212> TYPE: PRT
<213> ORGANISM: Artificial Sequence
<220> FEATURE:
<223> OTHER INFORMATION: RAM01c

<400> SEQUENCE: 10

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 11
<211> LENGTH: 448
<212> TYPE: PRT
<213> ORGANISM: Artificial Sequence
<220> FEATURE:
<223> OTHER INFORMATION: RAM9hc

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Ser Ile Gly Ser Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Gly Ser Gln Trp Leu Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial Sequence
<220> FEATURE:
<223> OTHER INFORMATION: RAM91c

<400> SEQUENCE: 12
```

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
                35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 13
<211> LENGTH: 457
<212> TYPE: PRT
<213> ORGANISM: Artificial Sequence
<220> FEATURE:
<223> OTHER INFORMATION: RAM4hc

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
                35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 14
<211> LENGTH: 214
<212> TYPE: PRT
<213> ORGANISM: Artificial Sequence
<220> FEATURE:
<223> OTHER INFORMATION: RAM41c

<400> SEQUENCE: 14

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

```
Ile Tyr Gly Thr Ser Ser Arg Ala Thr Gly Ile Pro Asp Arg Phe Ser
 50                  55                  60

Gly Ser Ala Ser Gly Thr Asp Phe Thr Leu Thr Ile Ser Arg Leu Gln
 65                  70                  75                  80

Pro Glu Asp Phe Ala Val Tyr Tyr Cys Gln Gln Tyr Gly Arg Ser Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 348
<212> TYPE: DNA
<213> ORGANISM: Cricetulus griseus
<220> FEATURE:
<221> NAME/KEY: CDS
<222> LOCATION: (1)..(348)

<400> SEQUENCE: 15 atg ccg atg ttc acc gtg aac acc aac gtt ccc cgc gcc tcc gtg cca        48
Met Pro Met Phe Thr Val Asn Thr Asn Val Pro Arg Ala Ser Val Pro
  1               5                  10                  15 gag ggg ctt ctc tcc gag ctc acc cag cag ctg gcg cag gcc acc ggc        96
Glu Gly Leu Leu Ser Glu Leu Thr Gln Gln Leu Ala Gln Ala Thr Gly
             20                  25                  30 aag ccg gcc cag tac atc gca gtg cac gtg gtc ccg gac cag ctc atg       144
Lys Pro Ala Gln Tyr Ile Ala Val His Val Val Pro Asp Gln Leu Met
         35                  40                  45 act ttt agc ggc tct agc gac ccc tgc gcc ctg tgc agc ctg cat agt       192
Thr Phe Ser Gly Ser Ser Asp Pro Cys Ala Leu Cys Ser Leu His Ser
     50                  55                  60 atc ggc aag atc ggc ggc gcg cag aac cgc acc tac agc aag ctg ctg       240
Ile Gly Lys Ile Gly Gly Ala Gln Asn Arg Thr Tyr Ser Lys Leu Leu
 65                  70                  75                  80 tgc ggc ctg ctg gct gat cgc ctg cac atc agc ccg gac cgg atc tac       288
Cys Gly Leu Leu Ala Asp Arg Leu His Ile Ser Pro Asp Arg Ile Tyr
                 85                  90                  95 atc aat tat tac gac atg agc gcg gcc aac gtg ggc tgg aac ggc tcc       336
Ile Asn Tyr Tyr Asp Met Ser Ala Ala Asn Val Gly Trp Asn Gly Ser
            100                 105                 110 acc ttc gct tga                                                       348
Thr Phe Ala
        115

<210> SEQ ID NO 16
<211> LENGTH: 115
```

<212> TYPE: PRT
<213> ORGANISM: Cricetulus griseus

<400> SEQUENCE: 16

Met Pro Met Phe Thr Val Asn Thr Asn Val Pro Arg Ala Ser Val Pro
1               5                   10                  15

Glu Gly Leu Leu Ser Glu Leu Thr Gln Gln Leu Ala Gln Ala Thr Gly
            20                  25                  30

Lys Pro Ala Gln Tyr Ile Ala Val His Val Val Pro Asp Gln Leu Met
        35                  40                  45

Thr Phe Ser Gly Ser Ser Asp Pro Cys Ala Leu Cys Ser Leu His Ser
    50                  55                  60

Ile Gly Lys Ile Gly Gly Ala Gln Asn Arg Thr Tyr Ser Lys Leu Leu
65                  70                  75                  80

Cys Gly Leu Leu Ala Asp Arg Leu His Ile Ser Pro Arg Ile Tyr
                85                  90                  95

Ile Asn Tyr Tyr Asp Met Ser Ala Ala Asn Val Gly Trp Asn Gly Ser
                100                 105                 110

Thr Phe Ala
        115

<210> SEQ ID NO 17
<211> LENGTH: 1368
<212> TYPE: DNA
<213> ORGANISM: Artificial Sequence
<220> FEATURE:
<223> OTHER INFORMATION: Heavy chain of A5

<400> SEQUENCE: 17
atggagactg ggctgcgctg gcttctcctg gtcgctgtgc tcaaaggtgt ccagtgtcag      60
tcggtggagg agtccggggg tcgcctggtc acgcctggga caccctgac  actcacctgc    120
acagtgtctg gattctccct cggcagctac gacatgagct gggtccgcca ggctccaggg    180
aagggactgg aatggatcgg agtgattttt actgatgata cacatacta  cgcgagctgg    240
gcgaaaggcc gattaccat  ctccaaagcc tcgtcgacca cggtggatct gaaaatcacc    300
agtccgacaa ccgaggacac ggccacctac ttctgttcca  aatttggttc tgtcggtgac    360
ttgtggggcc caggcaccct ggtcaccgtc tcctcagggc aacctaaggc tccatcagtc    420
ttcccactgg cccctgctg  cggggacaca cccagctcca cggtgaccct gggctgcctg    480
gtcaaaggct acctccgga  gccagtgacc gtgacctgga actcgggcac cctcaccaat    540
ggggtacgca ccttcccgtc cgtccggcag tcctcaggcc tctactcgct gagcagcgtg    600
gtgagcgtga cctcaagcag ccagcccgtc acctgcaacg tggcccaccc agccaccaac    660
accaaagtgg acaagaccgt tgcgccctcg acatgcagca agcccacgtg cccacccct   720
gaactcctgg ggggaccgtc tgtcttcatc ttccccccaa  acccaaagga caccctcatg    780
atctcacgca cccccgaggt cacatgcgtg gtggtggacg tgagccagga tgaccccgag    840
gtgcagttca catggtacat aaacaacgag caggtgcgca ccgcccggcc gccgctacgg    900
gagcagcagt tcaacagcac gatccgcgtg tcagcaccc  tccccatcgc gcaccaggac    960
tggctgaggg gcaaggagtt caagtgcaaa gtccacaaca aggcactccc ggcccccatc   1020
gagaaaacca tctccaaagc cagagggcag cccctggagc cgaaggtcta caccatgggc   1080
cctcccggg  aggagctgag cagcaggtcg gtcagcctga cctgcatgat caacggcttc   1140
tacccttccg acatctcggt ggagtgggag aagaacggga aggcagagga caactacaag   1200

-continued

```
accacgccgg ccgtgctgga cagcgacggc tcctacttcc tctacagcaa gctctcagtg    1260
cccacgagtg agtggcagcg gggcgacgtc ttcacctgct ccgtgatgca cgaggccttg    1320
cacaaccact acacgcagaa gtccatctcc cgctctccgg gtaaatga                 1368
```

<210> SEQ ID NO 18
<211> LENGTH: 455
<212> TYPE: PRT
<213> ORGANISM: Artificial Sequence
<220> FEATURE:
<223> OTHER INFORMATION: Heavy chain of A5

<400> SEQUENCE: 18

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Gly
        35                  40                  45

Ser Tyr Asp Met Ser Trp Val Arg Gln Ala Pro Gly Lys Gly Leu Glu
    50                  55                  60

Trp Ile Gly Val Ile Phe Thr Asp Asp Asn Thr Tyr Tyr Ala Ser Trp
65                  70                  75                  80

Ala Lys Gly Arg Phe Thr Ile Ser Lys Ala Ser Ser Thr Thr Val Asp
                85                  90                  95

Leu Lys Ile Thr Ser Pro Thr Thr Glu Asp Thr Ala Thr Tyr Phe Cys
            100                 105                 110

Ser Lys Phe Gly Ser Val Gly Asp Leu Trp Gly Pro Gly Thr Leu Val
        115                 120                 125

Thr Val Ser Ser Gly Gln Pro Lys Ala Pro Ser Val Phe Pro Leu Ala
    130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
        195                 200                 205

Pro Val Thr Cys Asn Val Ala His Pro Ala Thr Asn Thr Lys Val Asp
    210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
        275                 280                 285

Asn Glu Gln Val Arg Thr Ala Arg Pro Pro Leu Arg Glu Gln Gln Phe
    290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335
```

-continued

```
Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
        355                 360                 365

Arg Ser Val Ser Leu Thr Cys Met Ile Asn Gly Phe Tyr Pro Ser Asp
    370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
        435                 440                 445

Ile Ser Arg Ser Pro Gly Lys
    450                 455

<210> SEQ ID NO 19
<211> LENGTH: 711
<212> TYPE: DNA
<213> ORGANISM: Artificial Sequence
<220> FEATURE:
<223> OTHER INFORMATION: Light chain of A5

<400> SEQUENCE: 19
atggacacga gggcccccac tcagctgctg gggctcctgc tgctctggct cccaggtgcc      60
acatttgctc aagtgctgac ccagactcca tcctccgtgt ctgccgctgt gggaggcaca     120
gtcaccatca ctgccagtc cagtcagagt gtttatggtg caactactt atcctggtat      180
cagcagaaac cagggcagcc tcccaagctc ctgatctatg ctgcatccac tctggcatct     240
ggggtcccat cgcggttcaa aggcagtgga tctgggacac agttcactct cacaatcgcc     300
gaagtacagt gtgacgatgc tgccacttac tactgtcaag gtattttta tggtgttatt     360
aatagtttcg gcggagggac cgaggtggtg gtcaaaggtg atccagttgc acctactgtc     420
ctcatcttcc caccagctgc tgatcaggtg caactggaa cagtcaccat cgtgtgtgtg     480
gcgaataaat actttcccga tgtcaccgtc acctgggagg tggatggcac acccaaaca     540
actggcatcg agaacagtaa acaccgcag aattctgcag attgtaccta caacctcagc     600
agcactctga cactgaccag cacacagtac aacagccaca aagagtacac ctgcaaggtg     660
acccagggca cgacctcagt cgtccagagc ttcaataggg gtgactgtta g             711

<210> SEQ ID NO 20
<211> LENGTH: 236
<212> TYPE: PRT
<213> ORGANISM: Artificial Sequence
<220> FEATURE:
<223> OTHER INFORMATION: Light chain of A5

<400> SEQUENCE: 20

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Asn Cys Gln Ser Ser
        35                  40                  45

Gln Ser Val Tyr Gly Gly Asn Tyr Leu Ser Trp Tyr Gln Gln Lys Pro
    50                  55                  60
```

```
Gly Gln Pro Pro Lys Leu Leu Ile Tyr Ala Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ala Glu Val Gln Cys Asp Asp Ala Ala Thr Tyr Tyr Cys
            100                 105                 110

Gln Gly Tyr Phe Tyr Gly Val Ile Asn Ser Phe Gly Gly Gly Thr Glu
            115                 120                 125

Val Val Val Lys Gly Asp Pro Val Ala Pro Thr Val Leu Ile Phe Pro
            130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
            210                 215                 220

Thr Ser Val Val Gln Ser Phe Asn Arg Gly Asp Cys
225                 230                 235
```